United States Patent
Shimizu et al.

(10) Patent No.: US 10,183,905 B2
(45) Date of Patent: Jan. 22, 2019

(54) METHOD FOR PRODUCING ACETIC ACID

(71) Applicant: DAICEL CORPORATION, Osaka-shi, Osaka (JP)

(72) Inventors: Masahiko Shimizu, Himeji (JP); Nobuyuki Hirabayashi, Himeji (JP); Yoshihisa Mizutani, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 15/534,349

(22) PCT Filed: Sep. 20, 2016

(86) PCT No.: PCT/JP2016/077651
§ 371 (c)(1),
(2) Date: Jun. 8, 2017

(87) PCT Pub. No.: WO2017/057085
PCT Pub. Date: Apr. 6, 2017

(65) Prior Publication Data
US 2017/0349521 A1 Dec. 7, 2017

(30) Foreign Application Priority Data

Sep. 29, 2015 (JP) .................... 2015-192286

(51) Int. Cl.
| C07C 51/12 | (2006.01) |
| C07B 61/00 | (2006.01) |
| C07C 51/44 | (2006.01) |
| C07C 53/08 | (2006.01) |
| B01D 3/00 | (2006.01) |
| B01D 3/34 | (2006.01) |
| B01D 3/42 | (2006.01) |
| C01B 3/16 | (2006.01) |
| B01J 23/46 | (2006.01) |

(52) U.S. Cl.
CPC .............. *C07C 51/12* (2013.01); *B01D 3/009* (2013.01); *B01D 3/343* (2013.01); *B01D 3/4294* (2013.01); *C01B 3/16* (2013.01); *C07B 61/00* (2013.01); *C07C 51/44* (2013.01); *C07C 53/08* (2013.01); *B01J 23/464* (2013.01); *B01J 23/468* (2013.01)

(58) Field of Classification Search
CPC ......... C07C 51/12; C07C 51/44; C07C 53/08; B01D 3/009; B01D 3/343; B01D 3/4292; C01B 3/16; C07B 61/00; B01J 23/464; B01J 23/468
See application file for complete search history.

(56) References Cited

U.S. PATENT DOCUMENTS

| 5,576,458 A | 11/1996 | Minami et al. |
| 7,678,940 B2 * | 3/2010 | Miura ............... C07C 51/44 |
| | | 562/608 |
| 7,884,237 B2 * | 2/2011 | Shaver .............. C07C 51/12 |
| | | 562/519 |
| 7,884,241 B2 * | 2/2011 | Miura ............... C07C 51/44 |
| | | 562/608 |
| 2009/0036710 A1 | 2/2009 | Miura et al. |
| 2010/0121101 A1 * | 5/2010 | Shaver .............. C07C 51/12 |
| | | 562/519 |
| 2013/0264186 A1 | 10/2013 | Shimizu et al. |
| 2015/0025270 A1 | 1/2015 | Shimizu et al. |

FOREIGN PATENT DOCUMENTS

| EP | 1 912 926 | 4/2008 |
| EP | 2 657 220 A1 | 10/2013 |
| EP | 2 826 767 A1 | 1/2015 |
| JP | 7-309800 A | 11/1995 |
| JP | 2009-501129 A | 1/2009 |
| WO | WO 2012/086386 A1 | 6/2012 |
| WO | WO 2013/137236 A1 | 9/2013 |

OTHER PUBLICATIONS

International Search Report for PCT/JP2016/077651 (PCT/ISA/210) dated Nov. 22, 2016.
Written Opinion of the International Searching Authority for PCT/JP2016/077651 (PCT/ISA/237) dated Nov. 22, 2016.
English translation of the Written Opinion of the International Searching Authority (Forms PCT/IB/310 and PCT/ISA/237) dated Aug. 10, 2017, for corresponding International Application No. PCT/JP2016/077651.
European Office Action, dated Oct. 19, 2018, for European Application No. 16851259.8.

* cited by examiner

Primary Examiner — Pancham Bakshi
Assistant Examiner — Mark R Luderer
(74) Attorney, Agent, or Firm — Birch, Stewart, Kolasch & Birch, LLP

(57) ABSTRACT

A method produces acetic acid and includes a reaction step, a first purification step, a second purification step, and a third purification step. In the reaction step, a material mixture including methanol, carbon monoxide, a catalyst, and an iodide is subjected to a methanol carbonylation reaction in a reactor (1) to form acetic acid. In the first purification step, a crude acetic acid stream including acetic acid formed in the reaction step is subjected to distillation in a distillation column (3) to give a first acetic acid stream enriched with acetic acid. In the second purification step, the first acetic acid stream is subjected to distillation in a distillation column (5) to give a second acetic acid stream further enriched with acetic acid. In the third purification step, an acetic acid stream is subjected to purification in an additional purification unit (e.g., a distillation column (6)) while controlling the corrosive iodine concentration in the acetic acid stream passing through the unit to 100 ppm or less, to give a third acetic acid stream still further enriched with acetic acid. The method for producing acetic acid is suitable for restraining corrosion of the acetic acid production equipment.

26 Claims, 1 Drawing Sheet

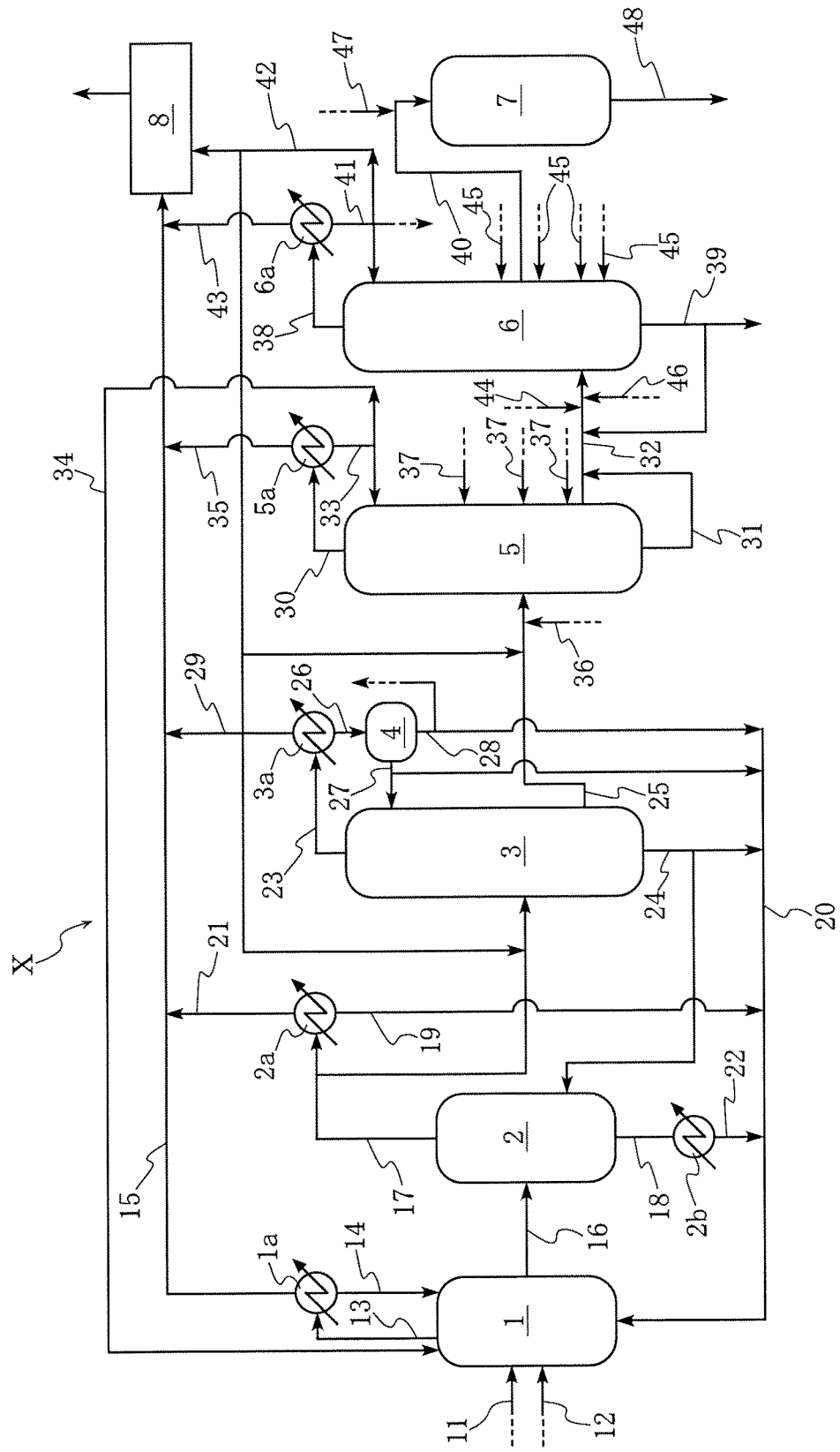

METHOD FOR PRODUCING ACETIC ACID

TECHNICAL FIELD

The present invention generally relates to methods for producing acetic acid. This application claims priority to Japanese Patent Application No. 2015-192286 filed Sep. 29, 2015, the entire contents of which are incorporated herein by reference.

BACKGROUND ART

A methanol carbonylation process is known as a acetic acid synthesizing process that is suitable for acetic acid industrial production. With this synthesizing process, starting materials methanol and carbon monoxide are reacted with each other in the presence of a predetermined catalyst to form acetic acid.

An acetic acid production plant for use in acetic acid production using the methanol carbonylation process includes two or more units such as a reactor, a flash evaporator, a low-boiling component removing column, and a dehydration column. In the acetic acid production plant as mentioned above, acetic acid is produced typically through processes in the individual units as follows. In the reactor, acetic acid is continuously formed from starting materials methanol and carbon monoxide by a methanol carbonylation reaction. In the flash evaporator, a reaction liquid from the reactor, where the reaction liquid contains acetic acid formed in the reactor, is subjected to a so-called flash evaporation treatment to extract vapor of crude acetic acid from the reaction liquid. In the low-boiling component removing column, the crude acetic acid is subjected to distillation, and a liquid acetic acid stream enriched with acetic acid is drawn out of the low-boiling component removing column. The distillation is performed mainly for removing low-boiling components from the crude acetic acid, where the low-boiling components have lower boiling points as compared with acetic acid. In the dehydration column, the acetic acid stream is subjected to distillation mainly for removing water from the acetic acid stream, and a liquid acetic acid stream further enriched with acetic acid is drawn out of the dehydration column.

The methanol carbonylation process may employ iodide as a promoter for assisting the action of a catalyst to be used. Iodine, when used, forms hydrogen iodide as a by-product in the reactor. The hydrogen iodide, with main product acetic acid and other substances, passes through the units in the acetic acid production plant, acts as a strong acid, and causes corrosion of the acetic acid production plant. Techniques for decreasing the hydrogen iodide concentration in the low-boiling component removing column can be found typically in PCT International Publication Number WO 2013/137236 (PTL 1). Techniques for decreasing the hydrogen iodide concentration in the dehydration column can be found typically in PCT International Publication Number WO 2012/086386 (PTL 2).

CITATION LIST

Patent Literature

PTL 1: PCT International Publication Number WO 2013/137236

PTL 2: PCT International Publication Number WO 2012/086386

SUMMARY OF INVENTION

Technical Problem

Assume that the acetic acid production plant that gives hydrogen iodide as a by-product in the reactor further includes a purification unit such as a distillation column downstream from the dehydration column. In this case, hydrogen iodide tends to be thickened (concentrated) in the additional purification unit even when the conventional techniques for decreasing the hydrogen iodide concentration are employed in the low-boiling component removing column and/or in the dehydration column. The thickening of hydrogen iodide in the additional purification unit causes corrosion of the acetic acid production equipment in the purification unit. The present invention has been made under these circumstances and has an object to provide an acetic acid production method which is suitable for restraining corrosion of such acetic acid production equipment.

Solution to Problem

The present invention provides a method for producing acetic acid in acetic acid production equipment, where the equipment includes a reactor, a first distillation column, a second distillation column, and an additional purification unit. The method includes a reaction step, a first purification step, a second purification step, and a third purification step. The reaction step is the step of subjecting a material mixture containing methanol, carbon monoxide, a catalyst, and an iodide to a methanol carbonylation reaction in the reactor to form acetic acid. The first purification step is the step of subjecting a crude acetic acid stream to distillation in the first distillation column to give a first acetic acid stream enriched with acetic acid as compared with the crude acetic acid stream, where the crude acetic acid stream includes acetic acid formed in the reaction step. The second purification step is the step of subjecting the first acetic acid stream to distillation in the second distillation column to give a second acetic acid stream enriched with acetic acid as compared with the first acetic acid stream. The third purification step is the step of subjecting an acetic acid stream to purification in the additional purification unit, where the acetic acid stream is the second acetic acid stream or is an acetic acid stream derived from the second acetic acid stream, while controlling the corrosive iodine concentration in the acetic acid stream passing through the unit to 100 ppm or less. This gives a third acetic acid stream enriched with acetic acid as compared with the second acetic acid stream. As used herein, the term "corrosive iodines" refers to both iodine in the form of hydrogen iodide, and iodine (iodine ions) as dissociated from a counter ion. Also as used herein, the term "corrosive iodine concentration" refers to the total of concentrations of these corrosive iodines. For example, the corrosive iodine concentration, when being on the order of part per million (ppm) (e.g., 1 ppm or more), may be determined typically by coulometric titration of a liquid containing corrosive iodines (iodine in the form of hydrogen iodide, and iodine ions) to be measured, where the titration is performed using a silver nitrate aqueous solution as a titrant. The corrosive iodine concentration, when being less than the order of ppm (e.g., less than 1 ppm), may be determined typically by arsenic-cerium catalytic spectrophotometry. The hydrogen iodide concentration, which constitutes part of the corrosive iodine concentration, may be determined typically by subtracting the concentration of metal ions in the liquid from the corrosive iodine concentration. This is a technique for deriving the concentration on the assumption that the counter ion of metal ions in the liquid is an iodine ion. The metal ions in the liquid are trace amounts of metal ions derived from components in the material mixture and trace amounts of free metal ions derived from (formed as a result of) corrosion of constitutional members or components of the equipment. Non-limiting examples of the metal ions include Fe, Ni, Cr, Co, Mo, Mn, Al, Zn, and Zr. The metal ion concentration may be determined typically by inductively coupled plasma (ICP) emission spectrometry. As used herein, the term "ppm" (part per million) refers to "ppm by mass".

The acetic acid production equipment, with which the method is performed, includes a reactor, a first distillation column, a second distillation column, and an additional purification unit. The additional purification unit is disposed downstream from the first and second distillation columns. The equipment may further include a flash evaporator disposed between the reactor and the first distillation column. The additional purification unit may be selected typically from distillation columns serving as so-called high-boiling component removing distillation columns, ion exchange resin columns, and distillation columns serving as so-called product columns or finishing columns. With the method, acetic acid formed in the reactor is subjected successively to two or more purification steps including the additional purification in the additional purification unit while controlling the corrosive iodine concentration in the additional purification unit of the acetic acid production equipment to 100 ppm or less. The method, as including the additional purification in the additional purification unit, is advantageous for offering high purity of the resulting product acetic acid. The third purification step in the additional purification unit, as performed with the control of the corrosive iodine concentration to 100 ppm or less, is suitable for restraining corrosion of the unit. Specifically, the third purification step as mentioned above, when performed, can eliminate or minimize the use of a nickel base alloy material or another highly corrosion-resistant but expensive material as a material constituting the inner wall of the additional purification unit, with which the third purification step is performed. Details of this will be described in after-mentioned working examples. The third purification step, when performed, can decrease the amount of the corrosion-resistant material to be used in the acetic acid production equipment.

As described above, the acetic acid production method is suitable for restraining corrosion of the additional purification unit and, consequently, is suitable for restraining corrosion of the acetic acid production equipment. The acetic acid production method, which is suitable for restraining corrosion of the acetic acid production equipment, is suitable for eliminating or minimizing the use of an expensive corrosion-resistant material in the equipment to reduce the cost in acetic acid production.

In a preferred embodiment, the additional purification unit includes a third distillation column, and the third purification step includes performing distillation in the third distillation column. This configuration is advantageous for offering high purity of the resulting product acetic acid.

In the embodiment where the additional purification unit includes the third distillation column, the third purification step preferably includes feeding at least one substance selected from the group consisting of methanol, methyl acetate, and potassium hydroxide to the acetic acid stream under the distillation in the third distillation column, so as to control the corrosive iodine concentration to 100 ppm or less. Methanol, when fed, can react with hydrogen iodide in the acetic acid stream to form methyl iodide and water. Methyl acetate, when fed, can react with hydrogen iodide in the acetic acid stream to form methyl iodide and acetic acid. Potassium hydroxide, when fed, can react with hydrogen iodide in the acetic acid stream to form potassium iodide and water. Decrease of the hydrogen iodide concentration in the acetic acid stream tends to also decrease the iodine ion concentration in the acetic acid stream. Methanol is fed to the acetic acid stream under the distillation in the third distillation column preferably at a level equal to or lower than the level at which the acetic acid stream is introduced into the third distillation column, where the levels are defined with respect to the height direction of the third distillation column. Methyl acetate is fed to the acetic acid stream under the distillation in the third distillation column preferably at a level equal to or lower than the level at which the acetic acid stream is introduced into the third distillation column, where the levels are defined with respect to the height direction of the third distillation column. Potassium hydroxide is fed to the acetic acid stream under the distillation in the third distillation column preferably at a level equal to or higher than the level at which the acetic acid stream is introduced into the third distillation column, where the levels are defined with respect to the height direction of the third distillation column. The configuration as described above is advantageous for efficiently controlling the corrosive iodine concentration in the acetic acid stream in the third distillation column to 100 ppm or less.

In the embodiment where the additional purification unit includes the third distillation column, the third purification step preferably includes, so as to control the corrosive iodine concentration to 100 ppm or less, at least one selected from the group consisting of recycling part of an overhead from the third distillation column to the first acetic acid stream before being introduced into the second distillation column, and recycling part of the overhead from the third distillation column to the crude acetic acid stream before being introduced into the first distillation column. As used herein, the term "overhead" from a distillation column refers to, of condensates, a portion that is not returned as a reflux liquid to the distillation column, but is removed from the distillation system in the distillation column. The condensates are obtained by condensing vapors drawn, as an overhead stream, out of the distillation column during distillation, where the condensing is performed using a condenser or any other device. Of the overhead from the third distillation column, corrosive iodines contained in the liquid stream to be recycled to the first acetic acid stream will undergo the second purification step in the second distillation column and the third purification step in the third distillation column again. Specifically, corrosive iodines contained in the liquid stream to be recycled to the first acetic acid stream will undergo a purification path (purification process) centered on the second distillation column and a purification path centered on the third distillation column again. The purification path centered on the second distillation column typically includes a channel to discharge iodine-containing chemical species from the equipment, where these species are derived from the corrosive iodines; and a channel to perform a reaction of hydrogen iodide with methanol or methyl acetate to form methyl iodide to thereby decrease hydrogen iodide. The purification path centered on the third distillation column typically includes a channel to discharge iodine-containing chemical species from the equipment, where the species are derived from the corrosive iodines, and where the iodine-containing chemical species are discharged as components in a bottom liquid from the third distillation column. Of the overhead from the third distillation column, corrosive iodines contained in the liquid stream to be recycled to the crude acetic acid stream have the opportunity of undergoing, again, the first purification step in the first distillation column, the second purification step in the second distillation column, and the third purification step in the third distillation column. Specifically, the corrosive iodines contained in the liquid stream to be recycled to the crude acetic acid stream have the opportunity of undergoing, again, the purification paths centered on the first, second, and third distillation columns. The purification path centered on the first distillation column typically includes a channel to discharge iodine-containing chemical species from the equipment, where the species are derived from the corrosive iodines; and a channel to perform a reaction of hydrogen iodide with methanol or methyl acetate to form methyl iodide to thereby decrease hydrogen iodide. These configurations relating to recycling of the corrosive iodines are advantageous for reducing the abundance of hydrogen iodide and iodine ion to thereby control the corrosive iodine concentration to 100 ppm or less in the acetic acid stream in the third distillation column, where the third distillation column is located downstream from the second distillation column in the purification system. The amount (removed distillate amount) of the distillate to be removed from the distillation system in the third distillation column is typically 0.01 to 30 mass percent, preferably 0.1 to 10 mass percent, more preferably 0.3 to 5 mass percent, and furthermore preferably 0.5 to 3 mass percent, relative to the total amount of the condensate.

Preferably, the acetic acid production equipment further includes a scrubber system. The scrubber system treats part of gaseous components evolved in the equipment to form a component to be recycled to the reactor; and a component to be discharged from the equipment. The configuration is advantageous for converting the corrosive iodines contained in gaseous components evolved in the acetic acid production equipment into methyl iodide to be recycled to the reactor. In addition, the configuration is advantageous for efficiently discharging other unnecessary chemical species from the equipment.

Preferably, part of the overhead from the third distillation column is introduced into the scrubber system. This configuration is advantageous typically for converting corrosive iodines contained in the overhead from the third distillation column into methyl iodide in the scrubber system and for recycling the methyl iodide to the reaction system to be reused therein. In addition, the configuration is still advantageous for discharging other unnecessary chemical species from the equipment using the scrubber system.

Preferably, the third purification step includes feeding at least one substance selected from the group consisting of methanol, methyl acetate, and potassium hydroxide to an acetic acid stream before being introduced into the additional purification unit, so as to control the corrosive iodine concentration to 100 ppm or less. Methanol, when fed, can react with hydrogen iodide in the acetic acid stream to form methyl iodide and water. Methyl acetate, when fed, can react with hydrogen iodide in the acetic acid stream to form methyl iodide and acetic acid. Potassium hydroxide, when fed, can react with hydrogen iodide in the acetic acid stream to form potassium iodide and water. Decrease of the hydrogen iodide concentration in the acetic acid stream tends to also decrease the iodine ion concentration in the acetic acid stream. The feeding to the acetic acid stream before being introduced into the additional purification unit is preferably performed so that the acetic acid stream before being introduced into the additional purification unit has a corrosive iodine concentration of 100 ppb or less. As used herein, the term "ppb" refers to "ppb by mass". This configuration is advantageous for efficiently controlling the corrosive iodine concentration in the acetic acid stream in the additional purification unit to 100 ppm or less.

Preferably, the acetic acid stream in the additional purification unit has a water concentration of 0.001 to 2 mass percent. The acetic acid stream in the additional purification unit may have a water concentration of preferably 0.001 mass percent or more, more preferably 0.003 mass percent or more, furthermore preferably 0.005 mass percent or more, and particularly preferably 0.006 mass percent or more. This is preferred from the viewpoint of allowing a passive film of an inner wall constitutional material to be appropriately formed on the inner wall surface of the unit upon the purification in the unit, to thereby restrain corrosion of the inner wall. The acetic acid stream in the additional purification unit may have a water concentration of preferably 2 mass percent or less, more preferably 1 mass percent or less, and furthermore preferably 0.5 mass percent or less. This is preferred from the viewpoint of restraining ionization (electrolytic dissociation) of hydrogen iodide and acetic acid in the liquid to be treated upon purification in the unit, to thereby restrain corrosion of the inner wall of the unit. The water concentration in the acetic acid stream in the additional purification unit is preferably appropriately controlled and managed typically from the above viewpoints. To control the water concentration in the acetic acid stream in the additional purification unit, water may be fed to an acetic acid stream before being introduced into the additional purification unit and/or to the acetic acid stream under the purification in the additional purification unit.

The purification in the additional purification unit may be performed at a temperature of preferably 160° C. or lower, more preferably 150° C. or lower, furthermore preferably 140° C. or lower, and still more preferably 120° C. or lower. This configuration is advantageous for reducing the rate of iodine-caused corrosion, which proceeds in the additional purification unit.

BRIEF DESCRIPTION OF DRAWINGS

The FIGURE schematically illustrates the general arrangement of acetic acid production equipment with which the acetic acid production method according to an embodiment of the present invention is performed.

DESCRIPTION OF EMBODIMENTS

The FIGURE schematically illustrates the general arrangement of the acetic acid production equipment X with which the acetic acid production method according to an embodiment of the present invention is performed. The acetic acid production equipment X includes a reactor 1, an evaporator 2, a distillation column 3, a decanter 4, a distillation column 5, a distillation column 6, an ion exchange resin column 7, a scrubber system 8, condensers 1a, 2a, 3a, 5a, and 6a, a heat exchanger 2b, and lines 11 to 48. The acetic acid production equipment X is configured so as to produce acetic acid continuously. The acetic acid production method according to the embodiment includes a reaction step, a flash evaporation step, a first distillation step, a second distillation step, a third distillation step, and an adsorption/removal step respectively performed in the reactor 1, the evaporator 2, the distillation column 3, the distillation column 5, the distillation column 6, and the ion exchange resin column 7, as illustrated below.

The reactor 1 is a unit with which the reaction step is performed. The reaction step is the step of performing a reaction (methanol carbonylation reaction) represented by Reaction Formula (1) to form acetic acid continuously. A reaction mixture, which is continuously stirred typically by a stirrer, is present in the reactor 1 during steady operation of the acetic acid production equipment X. The reaction mixture includes starting materials methanol and carbon monoxide, a catalyst, a promoter, water, target acetic acid to be produced, and various by-products. In the reaction mixture, a liquid phase and a gas phase (vapor phase) are in equilibrium. Reaction Formula (1) is expressed as follows:

[Chem. 1]

$$CH_3OH + CO \rightarrow CH_3COOH \qquad (1)$$

The starting materials in the reaction mixture are liquid methanol and gaseous carbon monoxide. The methanol is fed from a methanol reservoir (not shown) through the line 11 to the reactor 1 continuously at a predetermined flow rate. The carbon monoxide is fed from a carbon monoxide reservoir (not shown) through the line 12 to the reactor 1 continuously at a predetermined flow rate.

The catalyst in the reaction mixture plays the role of promoting the methanol carbonylation reaction. The catalyst may be selected typically from rhodium catalysts and iridium catalysts. A non-limiting example of the rhodium catalysts is a rhodium complex represented by the chemical formula $[Rh(CO)_2I_2]^-$. A non-limiting example of the iridium catalysts is an iridium complex represented by the chemical formula $[Ir(CO)_2I_2]^-$. The reaction mixture may have a catalyst concentration of typically 200 to 5000 ppm of the entire liquid phase in the reaction mixture.

The promoter is an iodide to assist the activity of the catalyst. Non-limiting examples of the iodide as the promoter include methyl iodide and an ionic iodide. The methyl iodide may offer the action of promoting the catalysis of the catalyst. The reaction mixture may have a methyl iodide concentration of typically 1 to 20 mass percent of the entire liquid phase in the reaction mixture. The ionic iodide is an iodide that forms an iodine ion in the reaction liquid. The ionic iodide may offer the actions of stabilizing the catalyst and of restraining side reactions. Non-limiting examples of the ionic iodide include lithium iodide, sodium iodide, and potassium iodide. The reaction mixture may have an ionic iodide concentration of typically 1 to 25 mass percent of the entire liquid phase in the reaction mixture.

Water in the reaction mixture is a component that is necessary for forming acetic acid in the reaction mechanism of the methanol carbonylation reaction, and is necessary for dissolving water-soluble components in the reaction system. The reaction mixture may have a water concentration of typically 0.1 to 15 mass percent of the entire liquid phase in the reaction mixture. The water concentration is preferably 15 mass percent or less for saving energy necessary for water removal in the acetic acid purification process so as to offer greater efficiency of acetic acid production. To control the water concentration, water may be fed to the reactor 1 continuously at a predetermined flow rate.

The acetic acid in the reaction mixture includes acetic acid previously charged into the reactor 1 before operation of the acetic acid production equipment X; and acetic acid formed as a main product of the methanol carbonylation reaction. The acetic acid can act as a solvent in the reaction system. The reaction mixture may have an acetic acid concentration of typically 50 to 90 mass percent, and preferably 60 to 80 mass percent, of the entire liquid phase in the reaction mixture.

A non-limiting example of major by-products in the reaction mixture is methyl acetate. The methyl acetate may be formed by the reaction between acetic acid and methanol. The reaction mixture may have a methyl acetate concentration of typically 0.1 to 30 mass percent of the entire liquid phase in the reaction mixture. Non-limiting examples of the by-products in the reaction mixture also include hydrogen iodide. The hydrogen iodide is formed inevitably in the reaction mechanism of the methanol carbonylation reaction when the catalyst and/or the promoter as above is used. The reaction mixture may have a hydrogen iodide concentration of typically 0.01 to 2 mass percent of the entire liquid phase in the reaction mixture. Non-limiting examples of the by-products also include hydrogen, methane, carbon dioxide, acetaldehyde, propionic acid, and alkyl iodides such as hexyl iodide and decyl iodide.

Reaction conditions in the reactor 1 housing the reaction mixture as above may be set typically as follows. The reaction temperature may be typically 150° C. to 250° C.; the reaction pressure as a total pressure may be typically 2.0 to 3.5 MPa (absolute pressure); and the carbon monoxide partial pressure may be typically 0.5 to 1.8 MPa (absolute pressure), and preferably 0.8 to 1.5 MPa (absolute pressure).

In the reactor 1 during equipment operation, various gas-phase components tend to be evolved or formed continuously with continuous formation of acetic acid to thereby increase the total volume of vapors. The vapors in the reactor 1 typically include carbon monoxide, hydrogen, methane, carbon dioxide, acetic acid, methyl acetate, methyl iodide, hydrogen iodide, acetaldehyde, and water. The vapors may be drawn out of the reactor 1 through the line 13. The inside pressure of the reactor 1 may be controlled by regulating the amount of the vapors to be drawn out. For example, the inside pressure of the reactor 1 may be held constant. The vapors drawn out of the reactor 1 are introduced into the condenser 1a.

The condenser 1a cools and partially condensates the vapors from the reactor 1 to separate the vapors into condensate components and gaseous components. The condensate components typically include acetic acid, methyl acetate, methyl iodide, acetaldehyde, and water and are introduced and recycled from the condenser 1a through the line 14 into the reactor 1. The gaseous components typically include carbon monoxide, hydrogen, methane, and carbon dioxide and are fed from the condenser 1a through the line 15 to the scrubber system 8. The gaseous components from the condenser 1a are separated in the scrubber system 8, from which useful components (e.g., carbon monoxide) are recovered. The separation and recovery in the embodiment is performed according to a wet process using an absorbing liquid (absorbent) to collect useful components from the gaseous components. The separation and recovery may also be performed using pressure swing adsorption. The separated, recovered useful components are recycled by introducing the same from the scrubber system 8 through a recycling line (not shown) into the reactor 1. The treatment in the scrubber system 8 and the subsequent recycling to the reactor 1 as mentioned above can be applied to after-mentioned gaseous components fed from other condensers to the scrubber system 8.

Acetic acid is continuously formed in the reactor 1 during equipment operation, as described above. The reaction mixture containing the acetic acid is continuously drawn out of the reactor 1 at a predetermined flow rate and fed through the line 16 into the subsequent (downstream) evaporator 2.

The evaporator 2 is a unit with which the flash evaporation step is performed. The flash evaporation step is the step of partially evaporating the reaction mixture to separate the mixture into vapors and residual liquid components, where the reaction mixture is continuously introduced into the evaporator 2. The evaporation may be performed by decompressing the reaction mixture without heating, or with heating. In the flash evaporation step, the vapor temperature may be typically 100° C. to 260° C.; the residual liquid component temperature may be typically 80° C. to 200° C.; and the internal pressure of the evaporator may be typically 50 to 1000 kPa (absolute pressure). The ratio (weight ratio) of the vapors to the residual liquid components, which are separated from each other in the flash evaporation step, is typically 10:90 to 50:50. The vapors formed in the step typically include acetic acid, methyl acetate, methyl iodide, water, hydrogen iodide, methanol, acetaldehyde, and propionic acid and are continuously drawn out of the evaporator 2 to the line 17. A part of the vapors drawn out of the evaporator 2 is continuously introduced into the condenser 2a, and another part (or the remainder) of the vapors is continuously introduced, as a crude acetic acid stream, into the subsequent distillation column 3. The crude acetic acid stream may have an acetic acid concentration of typically 87 to 99 mass percent. The residual liquid components formed in the step include the catalyst and the promoter contained in the reaction mixture; and acetic acid, methyl acetate, methyl iodide, water, and any other substances that remain without volatilization in the step. The residual liquid components are continuously introduced from the evaporator 2 through the line 18 into the heat exchanger 2b.

The condenser 2a cools and partially condenses the vapors from the evaporator 2 to separate the vapors into condensate components and gaseous components. The condensate components typically include acetic acid, methanol, methyl acetate, methyl iodide, acetaldehyde, and water and are introduced and recycled from the condenser 2a through the lines 19 and 20 into the reactor 1. The gaseous components typically include carbon monoxide and hydrogen and are fed from the condenser 2a through the lines 21 and 15 to the scrubber system 8. The acetic acid formation reaction in the reaction step is an exothermic reaction. A part of heat accumulated in the reaction mixture is transferred to the vapors derived from the reaction mixture in the flash evaporation step. The condensate components formed by cooling of the vapors in the condenser 2a are recycled to the reactor 1. Namely, the acetic acid production equipment X is capable of efficiently removing heat generated in the methanol carbonylation reaction, by the working of the condenser 2a.

The heat exchanger 2b cools the residual liquid components from the evaporator 2. The cooled residual liquid components are continuously introduced and recycled from the heat exchanger 2b through the lines 22 and 20 into the reactor 1.

The distillation column 3 is a unit with which the first distillation step is performed. The distillation column 3 in the embodiment is positioned as a so-called low-boiling component removing column. The first distillation step is the step of subjecting the vapors to distillation to purify acetic acid in the vapors, where the vapors are continuously introduced into the distillation column 3. The first distillation step corresponds typically to the first purification step in the present invention. The distillation column 3 may be selected typically from rectification columns such as plate columns and packed columns. The distillation column 3, when being a plate column, may contain typically 5 to 50 theoretical plates and may have a reflux ratio of typically 0.5 to 3000 according to the number of theoretical plates. In the interior of the distillation column 3 during the first distillation step, the column top pressure may be set typically at 80 to 160 kPa (gauge pressure), and the bottom pressure may be set typically at a pressure which is higher than the column top pressure and which is from 85 to 180 kPa (gauge pressure). In the interior of the distillation column 3 during the first distillation step, the column top temperature may be set typically at a temperature which is lower than the boiling temperature of acetic acid at the set column top pressure and which is from 90° C. to 130° C.; and the bottom temperature may be set typically at a temperature which is equal to or higher than the boiling point of acetic acid at the set bottom pressure and which is from 120° C. to 160° C.

Into the distillation column 3, the crude acetic acid stream (vapor) from the evaporator 2 is continuously introduced. At the distillation column 3 as above, vapors are continuously drawn out as an overhead stream from the column top to the line 23; a bottom liquid is continuously drawn out of the column bottom to the line 24; and a first acetic acid stream (liquid) as a side stream is continuously drawn out of the distillation column 3 at a height level between the column top and the column bottom, to the line 25.

The vapors drawn out of the column top of the distillation column 3 are enriched with low-boiling components as compared with the bottom liquid from the distillation column 3, where the low-boiling components have lower boiling points as compared with acetic acid. The vapors typically include methyl acetate, methyl iodide, hydrogen iodide, acetaldehyde, methanol, and water. The vapors also include acetic acid. The vapors as above are continuously introduced through the line 23 into the condenser 3a.

The condenser 3a cools and partially condenses the vapors from the distillation column 3 to separate the vapors into condensate components and gaseous components. The condensate components typically include methyl acetate, methyl iodide, hydrogen iodide, acetaldehyde, water, and acetic acid and are continuously introduced from the condenser 3a through the line 26 into the decanter 4. The condensate components introduced into the decanter 4 are separated into an aqueous phase and an organic phase. The aqueous phase includes water typically with methyl acetate, methyl iodide, hydrogen iodide, acetaldehyde, methanol, and acetic acid. The organic phase typically includes methyl acetate, acetaldehyde, methyl iodide, hydrogen iodide, methanol, and acetic acid. In the embodiment, a part of the aqueous phase is refluxed (returned) through the line 27 into the distillation column 3, and another part (or the remainder) of the aqueous phase is introduced and recycled through the lines 27 and 20 into the reactor 1. A part of the organic phase is introduced and recycled through the lines 28 and 20 into the reactor 1, and another part (or the remainder) of the organic phase is introduced through the line 28 into an acetaldehyde removing unit (not shown). The gaseous components separated in the condenser 3a typically include carbon monoxide, hydrogen, and hydrogen iodide and are fed from the condenser 3a through the lines 29 and 15 to the scrubber system 8. The hydrogen iodide in the gaseous components fed to the scrubber system 8 is absorbed by an absorbing liquid (absorbent) in the scrubber system 8 and reacts with methanol or methyl acetate in the absorbing liquid to form methyl iodide. Such a liquid containing useful components such as the methyl iodide is introduced or recycled from the scrubber system 8 through a recycling line (not shown) into the reactor 1, to be reused. A part of the condensate components formed by cooling in the condenser 3a is recycled via the decanter 4 to the reactor 1, as described above. This configuration allows the acetic acid production equipment X to efficiently remove heat by the working of the condenser 3a.

The bottom liquid drawn out of the bottom of the distillation column 3 is enriched with high-boiling components as compared with the overhead stream from the distillation column 3, where the high-boiling components have higher boiling points as compared with acetic acid. The bottom liquid typically includes propionic acid, and the catalyst and promoter as entrained. The bottom liquid also includes, for example, acetic acid, methyl iodide, methyl acetate, and water. In the embodiment, a part of the bottom liquid as above is continuously introduced and recycled through the line 24 into the evaporator 2, and another part (or the remainder) of the bottom liquid is continuously introduced and recycled through the lines 24 and 20 into the reactor 1.

The first acetic acid stream continuously drawn, as a side stream, out of the distillation column 3 is enriched with acetic acid as compared with the crude acetic acid stream continuously introduced into the distillation column 3. Specifically, the first acetic acid stream has an acetic acid concentration higher than the acetic acid concentration in the crude acetic acid stream. The acetic acid concentration in the first acetic acid stream may be typically 99 to 99.9 mass percent, as long as being higher than the acetic acid concentration in the crude acetic acid stream. The first acetic acid stream further includes other components such as methyl acetate, methyl iodide, water, and hydrogen iodide, in addition to acetic acid. In the embodiment, the first acetic acid stream is drawn out of the distillation column 3 at a level lower than the level at which the crude acetic acid stream is introduced into the distillation column 3, where the levels are defined with respect to the height direction of the distillation column 3. The first acetic acid stream from the distillation column 3 is introduced through the line 25 into the subsequent distillation column 5 continuously at a predetermined flow rate.

The distillation column 5 is a unit with which the second distillation step is performed. The distillation column 5 in the embodiment is positioned as a so-called dehydration column. The second distillation step is the step of subjecting the first acetic acid stream to distillation to further purify acetic acid, where the first acetic acid stream is continuously introduced into the distillation column 5. The second distillation step corresponds typically to the second purification step in the present invention. The distillation column 5 may be selected typically from rectification columns such as plate columns and packed columns. The distillation column 5, when being a plate column, may typically have 5 to 50 theoretical plates and may have a reflux ratio of typically 0.5 to 3000 according to the number of the theoretical plates. In the interior of the distillation column 5 during the second distillation step, the column top pressure may be set typically at 150 to 250 kPa (gauge pressure), and the bottom pressure may be set typically at a pressure which is higher than the column top pressure and which is from 160 to 290 kPa (gauge pressure). In the interior of the distillation column 5 during the second distillation step, the column top temperature may be set typically at a temperature which is higher than the boiling point of water and lower than the boiling point of acetic acid both at the set column top pressure, and which is from 130° C. to 155° C.; and the bottom temperature may be set typically at a temperature which is equal to or higher than the boiling point of acetic acid at the set bottom pressure and which is from 150° C. to 175° C.

Into the distillation column 5, the first acetic acid stream (liquid) is continuously introduced from the distillation column 3. At the distillation column 5 as above, vapors as an overhead stream are continuously drawn out of the column top to the line 30; and a bottom liquid is continuously drawn out of the column bottom to the line 31. Also at the distillation column 5, a side stream (liquid or gas) may be continuously drawn out to the line 32 at a height level between the column top and the column bottom.

The vapors drawn out of the top of the distillation column 5 are enriched with low-boiling components as compared with the bottom liquid from the distillation column 5, where the low-boiling components have lower boiling points as compared with acetic acid. Thus, the vapors typically include water, methyl acetate, methyl iodide, hydrogen iodide, and acetaldehyde. The vapors are continuously introduced through the line 30 into the condenser 5a.

The condenser 5a cools and partially condenses the vapors from the distillation column 5 to separate the vapors into condensate components and gaseous components. The condensate components typically include water and acetic acid. A part of the condensate components is continuously refluxed from the condenser 5a through the line 33 to the distillation column 5; and another part (or the remainder) of the condensate components is continuously introduced and recycled from the condenser 5a through the lines 33 and 34 into the reactor 1. This configuration allows the acetic acid production equipment X to efficiently remove heat at the condenser 5a. The gaseous components separated in the condenser 5a include carbon monoxide, hydrogen, carbon dioxide, methane, nitrogen, hydrogen iodide, and any other substances and are fed from the condenser 5a through the lines 35 and 15 to the scrubber system 8. Hydrogen iodide in the gaseous components coming into the scrubber system 8 is adsorbed by the absorbing liquid in the scrubber system 8 and reacts with methanol or methyl acetate in the absorbing liquid to form methyl iodide. Such a liquid containing useful components such as the methyl iodide is introduced or recycled from the scrubber system 8 through the recycling line (not shown) into the reactor 1, to be reused.

The bottom liquid drawn out of the bottom of the distillation column 5 is enriched with high-boiling components as compared with the overhead stream from the distillation column 5, where the high-boiling components have higher boiling points as compared with acetic acid. The bottom liquid typically includes propionic acid, and the catalyst and/or the promoter as entrained. The bottom liquid also includes acetic acid. The bottom liquid as above is fed through the line 31 to the line 32 to form a second acetic acid stream and is continuously introduced into the subsequent distillation column 6. Assume that the side stream is continuously drawn out of the distillation column 5 to the line 32. In this case, the side stream and the bottom liquid from the distillation column 5 are merged with each other to form the second acetic acid stream, and the resulting second acetic acid stream is continuously introduced into the subsequent distillation column 6.

The second acetic acid stream is enriched with acetic acid as compared with the first acetic acid stream continuously introduced into the distillation column 5. Specifically, the second acetic acid stream has an acetic acid concentration higher than the acetic acid concentration in the first acetic acid stream. The acetic acid concentration in the second acetic acid stream may be typically 99.1 to 99.99 mass percent, as long as being higher than the acetic acid concentration in the first acetic acid stream. The second acetic acid stream further includes other components such as methyl acetate, methyl iodide, water, and hydrogen iodide, in addition to acetic acid. In the embodiment, the side stream is drawn out of the distillation column 5 at a level lower than the level at which the first acetic acid stream is introduced into the distillation column 5, where the levels are defined with respect to the height direction of the distillation column 5.

In the acetic acid production equipment X, at least one substance selected from the group consisting of methanol, methyl acetate, and potassium hydroxide may be fed or added to the first acetic acid stream before being introduced through the line 25 into the distillation column 5, where the at least one substance is fed or added through the line 36, which is a supply line coupled to the line 25. This configuration is for the control of the corrosive iodine concentration of the second acetic acid stream from the distillation column 5 to 100 ppb or less. The amount of the at least one substance to be added may be determined typically on the basis of chemical composition analysis of a specimen sampled from the first acetic acid stream passing through the line 25. As used herein, the term "corrosive iodines" refers to both iodine in the form of hydrogen iodide, and iodine (iodine ion) as dissociated from a counter ion. Also as used herein, the term "corrosive iodine concentration" refers to the total of concentrations of these corrosive iodines. The corrosive iodine concentration may be determined typically by coulometric titration of a liquid containing corrosive iodines (iodine in hydrogen iodide, and iodine ions) to be measured, where the titration is performed using a silver nitrate aqueous solution as a titrant. The coulometric titration may be performed typically with an automatic titrator (trade name COM-1600, supplied by HIRANUMA SANGYO CORPORATION). The hydrogen iodide concentration, which constitutes part of the corrosive iodine concentration, may be determined typically by subtracting the concentration of metal ions in the liquid from the corrosive iodine concentration. This is a technique for deriving the concentration on the assumption that the counter ion of metal ions in the liquid is an iodine ion. The metal ions in the liquid are trace amounts of metal ions derived from components in the material mixture, and trace amounts of free metal ions derived from (caused by) corrosion of constitutional members of the equipment. Non-limiting examples of the metal ions include Fe, Ni, Cr, Co, Mo, Mn, Al, Zn, and Zr. The metal ion concentration may be determined typically by inductively coupled plasma (ICP) emission spectrometry.

Feeding of methanol to the first acetic acid stream tends to decrease hydrogen iodide in the first acetic acid stream. Specifically, when methanol is fed, the hydrogen iodide concentration in the first acetic acid stream may be decreased so that two chemical reactions represented by Reaction Formula (2) in the first acetic acid stream reach equilibrium, where the two chemical reactions are a reaction between methanol and hydrogen iodide to form methyl iodide and water, and a reverse reaction thereof. Decrease of the hydrogen iodide concentration in the first acetic acid stream tends to also decrease the iodine ion concentration in the first acetic acid stream. Reaction Formula (2) is expressed as follows:

[Chem. 2]

$$CH_3OH + HI \leftrightarrows CH_3I + H_2O \quad (2)$$

Feeding of methyl acetate to the first acetic acid stream tends to decrease hydrogen iodide in the first acetic acid stream. Specifically, when methyl acetate is fed, the hydrogen iodide concentration in the first acetic acid stream may be decreased so that two chemical reactions represented by Reaction Formula (3) reach equilibrium, where the two chemical reactions are a reaction between methyl acetate and hydrogen iodide to form methyl iodide and acetic acid, and a reverse reaction thereof. Reaction Formula (3) is expressed as follows:

[Chem. 3]

$$CH_3COOCH_3 + HI \leftrightarrows CH_3I + CH_3COOH \quad (3)$$

Feeding of potassium hydroxide to the first acetic acid stream tends to decrease hydrogen iodide in the first acetic acid stream. Specifically, when potassium hydroxide is fed, the hydrogen iodide concentration in the first acetic acid stream may be decreased so that two chemical reactions represented by Reaction Formula (4) reach equilibrium, where the two chemical reactions are a reaction between potassium hydroxide and hydrogen iodide to form potassium iodide and water, and a reverse reaction thereof. The chemical equilibrium lies far to the right in Reaction Formula (4). Reaction Formula (4) is expressed as follows:

[Chem. 4]

$$KOH + HI \leftrightarrows KI + H_2O \quad (4)$$

The feeding or addition action to the first acetic acid stream before being introduced into the distillation column 5, as described above, is preferred for lowering the hydrogen iodide concentration in the first acetic acid stream from the distillation column 3, so as to control the corrosive iodine concentration of the second acetic acid stream from the distillation column 5 to 100 ppb or less. In addition, the addition action contributes to a decreased abundance of hydrogen iodide in the distillation column 5 during distillation of the first acetic acid stream and thereby contributes to restrainment of thickening of hydrogen iodide and, in turn, to restrainment of thickening of corrosive iodine in the column top portion. The control of the corrosive iodine concentration in the distillation column 5 is advantageous for restraining corrosion in the distillation column 5.

In the embodiment, at least one substance selected from the group consisting of methanol, methyl acetate, and potassium hydroxide may be fed or added to the first acetic acid stream under the distillation in the distillation column 5, where the at least one substance is fed or added through the line 37, which is a supply line coupled to the distillation column 5. This configuration is for the control of the corrosive iodine concentration of the second acetic acid stream from the distillation column 5 to 100 ppb or less. The amount of the at least one substance to be added may be determined typically on the basis of chemical composition analysis of a specimen sampled from the first acetic acid stream passing through the line 25. Feeding of methanol to the first acetic acid stream under the distillation tends to decrease hydrogen iodide in the first acetic acid stream. Specifically, the feeding acts as described above with reference to Reaction Formula (2). Feeding of methyl acetate to the first acetic acid stream under the distillation tends to decrease hydrogen iodide in the first acetic acid stream. Specifically, the feeding acts as described above with reference to Reaction Formula (3). Feeding of potassium hydroxide to the first acetic acid stream under the distillation tends to decrease hydrogen iodide in the first acetic acid stream. Specifically, the feeding acts as described above with reference to Reaction Formula (4). The decrease of the hydrogen iodide concentration in the first acetic acid stream under the distillation in the distillation column 5 tends to also decrease the iodine ion concentration in the first acetic acid stream.

The levels of methanol and methyl acetate to be fed to the first acetic acid stream under the distillation in the distillation column 5 are preferably equal to or lower than the level at which the first acetic acid stream is introduced into the distillation column 5 (the level at which the line 25 is coupled to the distillation column 5), where the levels are defined with respect to the height direction of the distillation column 5. Methanol and methyl acetate have lower boiling points as compared with acetic acid and thereby tend to migrate to, and to be thickened in, the upper portion of the distillation column 5 during distillation. The methanol and methyl acetate are therefore preferably introduced into the distillation column 5 at levels equal to or lower than the level at which the first acetic acid stream is introduced, from the viewpoint of ensuring contact frequency of the substance with hydrogen iodide so as to efficiently decrease the hydrogen iodide concentration. In contrast, the level of potassium hydroxide to be fed to the first acetic acid stream under the distillation in the distillation column 5 is preferably equal to or higher than the level at which the first acetic acid stream is introduced into the distillation column 5, where the levels are defined with respect to the height direction of the distillation column 5. Potassium hydroxide has a higher boiling point as compared with acetic acid and thereby tends to migrate to, and to be thickened in, a lower portion in the distillation column 5 during distillation. The potassium hydroxide is therefore preferably introduced into the distillation column 5 at a level equal to or higher than the level at which the first acetic acid stream is introduced, from the viewpoint of ensuring contact frequency of the substance with hydrogen iodide so as to efficiently decrease the hydrogen iodide concentration.

The addition action to the first acetic acid stream in the distillation column 5, as described above, is preferred for the control of the corrosive iodine concentration in the second acetic acid stream from the distillation column 5 to 100 ppb or less. In addition, the addition action contributes to a decreased abundance of hydrogen iodide in the distillation column 5 during distillation of the first acetic acid stream and contributes typically to restrainment of thickening of hydrogen iodide and, in turn, to restrainment of thickening of corrosive iodine in the column top portion. The control of the corrosive iodine concentration in the distillation column 5 is advantageous for restraining corrosion in the distillation column 5.

The distillation column 6 is an additional purification unit with which the third distillation step is performed, and is positioned in the embodiment as a so-called high-boiling component removing column. The third distillation step is the step of subjecting the second acetic acid stream to purification to further purify acetic acid, with the control of the corrosive iodine concentration in the second acetic acid continuously introduced into the distillation column 6. The third distillation step may correspond to the third purification step in the present invention. The corrosive iodine concentration in the distillation column 6 is controlled to 100 ppm or less, preferably 30 ppm or less, more preferably 10 ppm or less, furthermore preferably 3.5 ppm or less, still more preferably 1 ppm or less, more preferably 0.3 ppm or less, more preferably 0.1 ppm or less, and particularly preferably 0.03 ppm or less. In the embodiment, the corrosive iodine concentration in the distillation column 6 may be typically 0.1 ppb or more. Each of the above-described addition actions to control the corrosive iodine concentration in the second acetic acid stream from the distillation column 5, namely, in the second acetic acid stream fed to the distillation column 6, to 100 ppb or less is preferred as techniques to achieve the corrosive iodine concentration in the distillation column 6 within the range as above. The distillation column 6 may be selected typically from rectification columns such as plate columns and packed columns. The distillation column 6, when being a plate column, may typically have 5 to 50 theoretical plates and may typically have a reflux ratio of 0.5 to 3000 according to the number of the theoretical plates. In the interior of the distillation column 6 during the third distillation step, the column top pressure may be set typically at a temperature of −100 to 150 kPa (gauge pressure), and the bottom pressure may be set typically at a pressure which is higher than the column top pressure and which is from −90 to 180 kPa (gauge pressure). In the interior of the distillation column 6 during the third distillation step, the column top temperature may be set typically at a temperature which is higher than the boiling point of water and lower than the boiling point of acetic acid both at the set column top pressure and which is from 50° C. to 150° C.; and the bottom temperature may be set typically at a temperature which is higher than the boiling point of acetic acid at the set bottom pressure and which is from 70° C. to 160° C. The column internal temperature is preferably 160° C. or lower, more preferably 150° C., furthermore preferably 140° C. or lower, and still more preferably 120° C. or lower. This is preferred from the viewpoint of restraining corrosion in the distillation column 6, where the corrosion is caused by corrosive iodines.

Into the distillation column 6, the second acetic acid stream (liquid) is continuously introduced from the distillation column 5. At the distillation column 6 as above, vapors as an overhead stream are continuously drawn out of the column top to the line 38; a bottom liquid is continuously drawn out of the column bottom to the line 39; and a side stream (liquid or gas) is continuously drawn out to the line 40 at a height level between the column top and the bottom of the distillation column 6. With respect to the height direction of the distillation column 6, the line 40 may be coupled to the distillation column 6 at a level lower than, or equal to, the level at which the line 32 is coupled to the distillation column 6, instead of the level shown in the FIGURE.

The vapors drawn out of the column top of the distillation column 6 are enriched with low-boiling components as compared with the bottom liquid from the distillation column 6, where the low-boiling components have lower boiling points as compared with acetic acid. The vapors typically include hydrogen iodide, methyl acetate, methyl iodide, water, and acetaldehyde. The vapors also include acetic acid. The vapors as above are continuously introduced through the line 38 into the condenser 6a.

The condenser 6a cools and partially condenses the vapors from the distillation column 6 to separate the vapors into condensate components and gaseous components. The condensate components typically include acetic acid and hydrogen iodide. At least part of the condensate components is continuously refluxed from the condenser 6a through the line 41 to the distillation column 6. A part (distillate) of the condensate components may be recycled from the condenser 6a through the lines 41 and 42 to the first acetic acid stream in the line 25 before being introduced into the distillation column 5. In addition to, or instead of this, a part (distillate)

of the condensate components may be recycled from the condenser 6a through the lines 41 and 42 to the crude acetic acid stream in the line 17 before being introduced into the distillation column 3. A part of the distillate from the condenser 6a may be fed to the scrubber system 8 and be used as an absorbing liquid in the system. At the scrubber system 8, hydrogen iodide and other gaseous components are separated from the distillate and are discharged from the equipment; and a liquid containing useful components is introduced or recycled from the scrubber system 8 through the recycling line (not shown) into the reactor 1 to be reused. The useful components include acetic acid and methyl iodide. The methyl iodide includes methyl iodide formed by the reaction of hydrogen iodide with methanol or methyl acetate in the absorbing liquid. In addition, a part of the distillate from the condenser 6a may be introduced through a line (not shown) into various pumps (not shown) operated in the equipment and is used as a sealant (sealing liquid) for the pumps. Further, a part of the distillate from the condenser 6a may be drawn out of the equipment steadily, or non-steadily as needed. The drawing is performed through a drawing line attached to the line 41. Assume that a part (distillate) of the condensate components is removed from the distillation system in the distillation column 6. In this case, the amount (removed distillate amount) of the distillate is typically 0.01 to 30 mass percent, preferably 0.1 to 10 mass percent, more preferably 0.3 to 5 mass percent, and furthermore preferably 0.5 to 3 mass percent, of the condensate formed in the condenser 6a. In contrast, the gaseous components separated in the condenser 6a typically include carbon monoxide, hydrogen, carbon dioxide, methane, nitrogen, and hydrogen iodide and are fed from the condenser 6a through the lines 43 and 15 to the scrubber system 8.

The bottom liquid drawn out of the bottom of the distillation column 6 through the line 39 is enriched with high-boiling components as compared with the overhead stream from the distillation column 6, where the high-boiling components have higher boiling points as compared with acetic acid. The bottom liquid typically includes propionic acid. The bottom liquid drawn out of the bottom of the distillation column 6 through the line 39 also includes corrodible metals which are formed in, and liberated from, the inner wall of members or components constituting the acetic acid production equipment X; and compounds between iodine and the corrodible metals, where the iodine is derived from corrosive iodines. The bottom liquid as above is discharged from the acetic acid production equipment X in the embodiment. Instead of this, it is also acceptable that a part of the bottom liquid is discharged from the equipment and another part (or the remainder) of the bottom liquid is recycled to the line 25.

The side stream continuously drawn out of the distillation column 6 to the line 40 is continuously introduced, as a third acetic acid stream, into the subsequent ion exchange resin column 7. The third acetic acid stream is enriched with acetic acid as compared with the second acetic acid stream continuously introduced into the distillation column 6. Specifically, the third acetic acid stream has an acetic acid concentration higher than the acetic acid concentration in the second acetic acid stream. The third acetic acid stream may have an acetic acid concentration of typically 99.8 to 99.999 mass percent, as long as being higher than the acetic acid concentration in the second acetic acid stream. In the embodiment, the side stream is drawn out of the distillation column 6 at a level higher than the level at which the second acetic acid stream is introduced into the distillation column 6, where the levels are defined with respect to the height direction of the distillation column 6. In another embodiment, the side stream is drawn out of the distillation column 6 at a level lower than the level at which the second acetic acid stream is introduced into the distillation column 6, where the levels are defined with respect to the height direction of the distillation column 6.

In the embodiment, at least one substance selected from the group consisting of methanol, methyl acetate, and potassium hydroxide may be fed or added to the second acetic acid stream before being introduced through the line 32 into the distillation column 6, where the at least one substance is fed or added through the line 44, which is a supply line coupled to the line 32. This is performed so as to control the corrosive iodine concentration in the second acetic acid stream in the distillation column 6 to 100 ppm or less. The amount of the at least one substance to be added may be determined typically on the basis of chemical composition analysis of a specimen sampled from the second acetic acid stream passing through the line 32. Feeding of methanol to the second acetic acid stream tends to decrease hydrogen iodide in the second acetic acid stream. Specifically, the feeding acts as described above on the feeding of methanol to the first acetic acid stream with reference to Reaction Formula (2). Feeding of methyl acetate to the second acetic acid stream tends to decrease hydrogen iodide in the second acetic acid stream. Specifically, the feeding acts as described above on the feeding of methyl acetate to the first acetic acid stream with reference to Reaction Formula (3). Feeding of potassium hydroxide to the second acetic acid stream tends to decrease hydrogen iodide in the second acetic acid stream. Specifically, the feeding acts as described above on the feeding of potassium hydroxide to the first acetic acid stream with reference to Reaction Formula (4). Decrease of hydrogen iodide, namely decrease of the hydrogen iodide concentration, in the second acetic acid stream tends to also decrease the iodine ion concentration in the second acetic acid stream.

The feeding or addition action to the second acetic acid stream before being introduced into the distillation column 6, as described above, can control the corrosive iodine concentration in the second acetic acid stream before being introduced into the distillation column 6 typically to 100 ppb or less. The addition action controls the corrosive iodine concentration in the second acetic acid stream preferably to 10 ppb or less. The addition action as above is preferred for decreasing the thickening of corrosive iodines in the second acetic acid stream in the distillation column 6, so as to control the corrosive iodine concentration in the second acetic acid stream in the distillation column 6 to 100 ppm or less. The addition action as above is preferred because the action can directly efficiently control the corrosive iodine concentration in the second acetic acid stream introduced into the distillation column 6.

In the embodiment, at least one substance selected from the group consisting of methanol, methyl acetate, and potassium hydroxide may be fed or added to the second acetic acid stream under the distillation in the distillation column 6, where the at least one substance is fed or added through the line 45, which is a supply line coupled to the distillation column 6. This is performed so as to control the corrosive iodine concentration in the second acetic acid stream in the distillation column 6 to 100 ppm or less. The amount of the at least one substance to be added may be determined typically on the basis of chemical composition analysis of a specimen sampled from the second acetic acid stream passing through the line 32. Feeding of methanol to the second acetic acid stream under the distillation tends to decrease hydrogen iodide in the second acetic acid stream. Specifically, the feeding acts as described above on the feeding of methanol to the first acetic acid stream with reference to Reaction Formula (2). Feeding of methyl acetate to the second acetic acid stream under the distillation tends to decrease hydrogen iodide in the second acetic acid stream. Specifically, the feeding acts as described above on the feeding of methyl acetate to the first acetic acid stream with reference to Reaction Formula (3). Feeding of potassium hydroxide to the second acetic acid stream under the distillation tends to decrease hydrogen iodide in the second acetic acid stream. Specifically, the feeding acts as described above on the feeding of potassium hydroxide to the first acetic acid stream with reference to Reaction Formula (4). Decrease of the hydrogen iodide concentration in the second acetic acid stream under the distillation in the distillation column 6 tends to also decrease the iodine ion concentration in the second acetic acid stream.

Levels at which methanol and methyl acetate are fed to the second acetic acid stream under the distillation in the distillation column 6 are each preferably equal to or lower than the level at which the second acetic acid stream is introduced into the distillation column 6 (the level at which the line 32 is coupled to the distillation column 6), where the levels are defined with respect to the height direction of the distillation column 6. Methanol and methyl acetate have lower boiling points as compared with acetic acid and thereby tend to migrate to, and to be thickened in, an upper portion in the distillation column 6 during distillation. The methanol and methyl acetate are therefore introduced into the distillation column 6 preferably at levels equal to or lower than the level at which the second acetic acid stream is introduced, where the levels are defined with respect to the height direction, from the viewpoint of ensuring contact frequency of the substance with hydrogen iodide so as to efficiently decrease the hydrogen iodide concentration. The levels at which methanol and methyl acetate are fed to the second acetic acid stream under the distillation in the distillation column 6 are preferably higher than the level of the line 40. This is preferred from the viewpoints of higher purity of the third acetic acid stream drawn out to the line 40 and, in turn, for higher purify of the product acetic acid. In contrast, the level at which potassium hydroxide is fed to the second acetic acid stream under the distillation in the distillation column 6 is preferably equal to or higher than the level at which the second acetic acid stream is introduced into the distillation column 6, where the levels are defined with respect to the height direction of the distillation column 6. Potassium hydroxide has a higher boiling point as compared with acetic acid and tends to migrate to, and to be thickened in, a lower portion in the distillation column 6 during distillation. The potassium hydroxide is therefore preferably introduced into the distillation column 6 at a level equal to or higher than the level at which the second acetic acid stream is introduced, from the viewpoint of ensuring contact frequency of the substance with hydrogen iodide so as to efficiently decrease the hydrogen iodide concentration. The potassium hydroxide is fed to the second acetic acid stream under the distillation in the distillation column 6 preferably at a level lower than the level of the line 40. This is preferred from the viewpoints of higher purity of the third acetic acid stream drawn out to the line 40 and, in turn, for higher purity of the product acetic acid.

Each of the above-described addition actions to the second acetic acid stream in the distillation column 6 is preferred for the control of the corrosive iodine concentration in the second acetic acid stream in the distillation column 6 to 100 ppm or less.

In the acetic acid production equipment X, water may be fed or added to the second acetic acid stream before being introduced through the line 32 into the distillation column 6, where the water is fed or added through the line 46, which is a supply line coupled to the line 32, so as to control the water concentration in the second acetic acid stream in the distillation column 6 to 0.001 to 2 mass percent. The amount of water to be added may be determined typically on the basis of chemical composition analysis of a specimen sampled from the second acetic acid stream passing through the line 32. The second acetic acid stream in the distillation column 6 has a water concentration of preferably 0.001 mass percent or more, more preferably 0.002 mass percent or more, furthermore preferably 0.003 mass percent or more, and particularly preferably 0.05 mass percent or more. This is preferred from the viewpoint of appropriately forming a passive film of an inner wall constitutional material on the inner wall surface of the distillation column 6, so as to restrain corrosion of the inner wall upon the distillation in the distillation column 6. The second acetic acid stream in the distillation column 6 has a water concentration of preferably 2 mass percent or less, more preferably 1 mass percent or less, and furthermore preferably 0.5 mass percent or less. This is preferred from the viewpoint of restraining ionization of hydrogen iodide and acetic acid in the liquid to be treated, so as to restrain corrosion of the inner wall of the distillation column 6 upon the distillation in the distillation column 6.

In the acetic acid production equipment X, a part of the overhead from the distillation column 6 may be recycled through the lines 41 and 42 to the first acetic acid stream before being introduced into the distillation column 5 so as to control the corrosive iodine concentration in the second acetic acid stream in the distillation column 6 to 100 ppm or less. In this configuration, of the overhead from the distillation column 6, corrosive iodines contained in the liquid stream to be recycled to the first acetic acid stream will again undergo the second distillation step in the distillation column 5 and the third distillation step in the distillation column 6. Specifically, corrosive iodines contained in the liquid stream to be recycled to the first acetic acid stream will again undergo a purification path centered on the distillation column 5 and a purification path centered on the distillation column 6. In the embodiment, the purification path centered on the distillation column 5 includes a channel to perform a reaction of hydrogen iodide with methanol or methyl acetate to form methyl iodide in the scrubber system 8 to thereby decrease hydrogen iodide; and a channel to discharge iodine-containing chemical species through the scrubber system 8 out of the equipment, where the chemical species are derived from corrosive iodines. In the embodiment, the purification path centered on the distillation column 6 includes the channel to perform a reaction of hydrogen iodide with methanol or methyl acetate to form methyl iodide to decrease hydrogen iodide in the scrubber system 8; and a channel to discharge compounds between corrodible metals and iodines from the distillation column 6 through the line 39 out of the equipment, where the iodines are derived from corrosive iodines. In addition to, or instead of, the recycling to the first acetic acid stream as above, a part of the overhead from the distillation column 6 may be recycled through the lines 41 and 42 to the crude acetic acid stream before being introduced into the distillation column 3 in the acetic acid production equipment X. This is performed so as to control the corrosive iodine concentration in the second acetic acid stream in the distillation column 6 to 100 ppm or less. Of the overhead from the distillation column 6, corrosive iodines contained in the liquid stream to be recycled to the crude acetic acid stream will again undergo the first purification step in the distillation column 3, the second purification step in the distillation column 5, and the third purification step in the distillation column 6. Specifically, the corrosive iodines contained in the liquid stream to be recycled to the crude acetic acid stream will again undergo purification paths centered on the distillation columns 3, 5, and 6. In the embodiment, the purification path centered on the distillation column 3 includes the channel to perform a reaction of hydrogen iodide with methanol or methyl acetate to form methyl iodide to thereby decrease hydrogen iodide in the scrubber system 8; and the channel to discharge iodine-containing chemical species through the scrubber system 8 out of the equipment, where the chemical species are derived from corrosive iodines. Assume that the liquid stream to be recycled from the distillation columns 3 and 5 to the reactor 1 includes corrosive iodines. In this case, the corrosive iodines have the opportunity of again undergoing the purification paths centered on the distillation columns 3, 5, and 6, where the channels include a channel to convert the corrosive iodines into methyl iodide. The configuration as above is advantageous for decreasing the abundances of hydrogen iodide and iodine ions to control the corrosive iodine concentration to 100 ppm or less, in the acetic acid stream (second acetic acid stream) in the distillation column 6, which is located downstream from the distillation column 5 in the purification system.

The ion exchange resin column 7 is an additional purification unit with which the adsorption/removal step is performed. The adsorption/removal step is the step of removing, via adsorption, mainly alkyl iodides (such as hexyl iodide and decyl iodide) from the third acetic acid stream to further purify acetic acid, where the third acetic acid stream is continuously introduced into the ion exchange resin column 7. The adsorption/removal step is the step of subjecting the third acetic acid stream to purification with the control of the corrosive iodine concentration to 100 ppm or less in the third acetic acid stream continuously introduced into the ion exchange resin column 7, to further purify acetic acid. The adsorption/removal step may therefore correspond to the third purification step in the present invention. An ion exchange resin capable of adsorbing alkyl iodides is packed in the ion exchange resin column 7, to form an ion exchange resin bed in the column. Non-limiting examples of the ion exchange resin include cation-exchange resins in which part of leaving protons in exchange groups such as sulfonic groups, carboxy groups, and phosphonate groups is replaced with a metal such as silver and/or copper. In the adsorption/removal step, the third acetic acid stream (liquid) passes through the interior of the ion exchange resin column 7 typically packed with the ion exchange resin, and, during the passing process, impurities such as alkyl iodides are adsorbed by the ion exchange resin and thereby removed from the third acetic acid stream. In the ion exchange resin column 7 during the adsorption/removal step, the inside temperature is typically 18° C. to 100° C., and the acetic acid stream passes through the column at a flow rate of typically 3 to 15 bed volume per hour.

Into the ion exchange resin column 7, the third acetic acid stream (liquid) from the distillation column 6 is continuously introduced. At the ion exchange resin column 7 as above, a fourth acetic acid stream is continuously drawn out of an lower end portion of the column to the line 48. The fourth acetic acid stream has a higher acetic acid concentration than the acetic acid concentration in the third acetic acid stream. Specifically, the fourth acetic acid stream is enriched with acetic acid as compared with the third acetic acid stream continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream may be stored in a product tank (not shown).

In the acetic acid production equipment X, water may be fed or added to the third acetic acid stream before being introduced through the line 40 into the ion exchange resin column 7, where the water is fed or added through the line 47, which is a supply line coupled to the line 40. This is performed so as to control the water concentration of the third acetic acid stream passing through the ion exchange resin column 7 to 0.001 to 2 mass percent. The amount of water to be added may be determined typically on the basis of chemical composition analysis of a specimen sampled from the third acetic acid stream passing through the line 40. The third acetic acid stream in the ion exchange resin column 7 has a water concentration of preferably 0.001 mass percent or more, more preferably 0.002 mass percent or more, furthermore preferably 0.003 mass percent or more, and particularly preferably 0.005 mass percent or more. This is preferred from the viewpoint of appropriately forming a passive film of an inner wall constitutional material on the inner wall surface of the column, so as to restrain corrosion of the inner wall upon the purification in the column. The third acetic acid stream in the ion exchange resin column 7 has a water concentration of preferably 2 mass percent or less, more preferably 1 mass percent or less, and furthermore preferably 0.5 mass percent or less. This is preferred from the viewpoint of restraining ionization of hydrogen iodide and acetic acid in the liquid to be treated upon the purification in the column, so as to restrain corrosion of the inner wall of the column.

The acetic acid production equipment X may further include a so-called product column or finishing column, which is a distillation column. The product column herein serves as an additional purification unit to further purify the fourth acetic acid stream fed from the ion exchange resin column 7. With the product column, a step as follows may be performed. This step is the step of subjecting the fourth acetic acid stream to purification so as to further purify acetic acid, while controlling the corrosive iodine concentration in the fourth acetic acid stream to 100 ppm or less, where the fourth acetic acid stream is continuously introduced into the product column. This step may correspond to the third purification step in the present invention. The product column, when provided, may be selected typically from rectification columns such as plate columns and packed columns. The product column, when being a plate column, may typically have 5 to 50 theoretical plates and may have a reflux ratio of typically 0.5 to 3000 according to the number of the theoretical plates. In the interior of the product column during the purification step, the column top pressure may be set at −195 to 150 kPa (gauge pressure), and the bottom pressure may be set typically at a pressure which is higher than the column top pressure and which is from −190 to 180 kPa (gauge pressure). In the interior of the product column during the purification step, the column top temperature may be set typically at a temperature which is higher than the boiling point of water and lower than the boiling point of acetic acid both at the set column top pressure and which is from 50° C. to 150° C., and the bottom temperature may be set typically at a temperature which is higher than the boiling point of acetic acid at the set bottom pressure and which is from 70° C. to 160° C. The column internal temperature is preferably 160° C. or lower, more preferably 150° C. or lower, furthermore preferably 140° C. or lower, and still more preferably 120° C. or lower. This is preferred from the viewpoint of restraining corrosion in the product column, caused by corrosive iodines. The treatment on the fourth acetic acid stream in the product column may be performed typically in the following manner.

The whole or part of the fourth acetic acid stream (liquid) from the ion exchange resin column 7 is continuously introduced into the product column. At the product column, vapors as an overhead stream including trace amounts of low-boiling components are continuously drawn out of the column top. The vapors are separated into condensate components and gaseous components in a predetermined condenser. A part of the condensate components is continuously refluxed to the product column; another part (or the remainder) of the condensate components is recycled to the reactor 1; and the gaseous components are fed to the scrubber system 8. Also at the product column, a bottom liquid containing trace amounts of high-boiling components is continuously drawn out of the column bottom and is recycled typically to the second acetic acid stream in the line 32 before being introduced into the distillation column 6. A side stream (liquid) as a fifth acetic acid stream is continuously drawn out of the product column at a height level between the column top and the column bottom. The side stream is drawn out of the product column typically at a level lower than the level at which the fourth acetic acid stream is introduced into the product column, where the levels are defined with respect to the height direction of the product column. The fifth acetic acid stream is enriched with acetic acid as compared with the fourth acetic acid stream continuously introduced into the product column. Specifically, the fifth acetic acid stream has an acetic acid concentration higher than the acetic acid concentration in the fourth acetic acid stream. The acetic acid concentration in the fifth acetic acid stream may be typically 99.9 to 99.999 mass percent, or more, as long as being higher than the acetic acid concentration in the fourth acetic acid stream. The fifth acetic acid stream may be stored typically in a product tank (not shown).

In an embodiment where the product column is provided, potassium hydroxide may be added to the fourth acetic acid stream before being introduced into the product column, so as to control the corrosive iodine concentration of the fourth acetic acid stream in the product column to 100 ppm or less. The amount of potassium hydroxide to be added may be determined typically on the basis of chemical composition analysis of a specimen sampled from the fourth acetic acid stream before being introduced into the product column. Feeding of potassium hydroxide to the fourth acetic acid stream tends to decrease hydrogen iodide in the fourth acetic acid stream. Specifically, the feeding acts as described above on the feeding of potassium hydroxide to the second acetic acid stream with reference to Reaction Formula (4). Decrease of hydrogen iodide, namely decrease of the hydrogen iodide concentration, in the fourth acetic acid stream tends to also decrease the iodine ion concentration in the fourth acetic acid stream. The addition action to the fourth acetic acid stream before being introduced into the product column may control the corrosive iodine concentration in the fourth acetic acid stream before being introduced into the product column typically to 100 ppb or less. The addition action may control the corrosive iodine concentration in the fourth acetic acid stream to a level of preferably 10 ppb or less, more preferably 2 ppb or less, and furthermore preferably 1 ppb or less. Such an addition action is preferred for restraining thickening of corrosive iodines in the fourth acetic acid stream in the product column, so as to control the corrosive iodine concentration in the fourth acetic acid stream to 100 ppm or less. The addition action as above is preferred from the viewpoint of directly and efficiently controlling the corrosive iodine concentration in the fourth acetic acid stream to be introduced into the product column.

In the embodiment where the product column is provided, potassium hydroxide may be fed or added to the fourth acetic acid stream under the distillation in the product column so as to control the corrosive iodine concentration in the fourth acetic acid stream in the product column to 100 ppm or less. The amount of potassium hydroxide to be added may be determined typically on the basis of chemical composition analysis of a specimen sampled from the fourth acetic acid stream before being introduced into the product column. Feeding of potassium hydroxide to the fourth acetic acid stream under the distillation tends to decrease hydrogen iodide in the fourth acetic acid stream. Specifically, the feeding acts as described above on the feeding of potassium hydroxide to the second acetic acid stream with reference to Reaction Formula (4). Decrease of the hydrogen iodide concentration in the fourth acetic acid stream under the distillation in the product column tends to also decrease the iodine ion concentration in the fourth acetic acid stream. Potassium hydroxide is fed to the fourth acetic acid stream under the distillation in the product column preferably at a level equal to or higher than the level at which the fourth acetic acid stream is introduced into the product column, where the levels are defined with respect to the height direction of the product column. Potassium hydroxide has a higher boiling point as compared with acetic acid and therefore tends to migrate to, and to be thickened in, a lower portion in the product column during distillation. Thus, potassium hydroxide is preferably introduced into the product column at a level equal to or higher than the level at which the fourth acetic acid stream is introduced, from the viewpoint of ensuring contact frequency of the substance with hydrogen iodide so as to efficiently decrease the hydrogen iodide concentration. In addition, potassium hydroxide is fed to the fourth acetic acid stream under the distillation in the product column preferably at a level lower than the level at which the fifth acetic acid stream is drawn out of the product column. This is preferred from the viewpoints of higher purity of the fifth acetic acid stream drawn out of the column and, in turn, for higher purity of the product acetic acid. The addition action to the fourth acetic acid stream in the product column, as described above, is preferred for controlling the corrosive iodine concentration in the fourth acetic acid stream in the product column to 100 ppm or less.

In the embodiment where the product column is provided, water may be fed or added to the fourth acetic acid stream before being introduced into the product column so as to control the water concentration in the fourth acetic acid stream in the product column to 0.001 to 2 mass percent. The amount of water to be added may be determined typically on the basis of chemical composition analysis of a specimen sampled from the fourth acetic acid stream before being introduced into the product column. The fourth acetic acid stream in the product column has a water concentration of preferably 0.001 mass percent or more, more preferably 0.002 mass percent or more, furthermore preferably 0.003 mass percent or more, and particularly preferably 0.05 mass percent or more. This is preferred from the viewpoint of appropriately forming a passive film of an inner wall constitutional material on the inner wall surface of the product column, so as to restrain corrosion of the inner wall during distillation in the product column. The fourth acetic acid stream in the product column has a water concentration of preferably 2 mass percent or less, more preferably 1 mass percent or less, and furthermore preferably 0.5 mass percent or less, from the viewpoint of restraining ionization of hydrogen iodide and acetic acid in the liquid to be treated, so as to restrain corrosion of the inner wall of the product column during distillation in the product column.

The acetic acid production method continuously performs a plurality of purification steps on acetic acid formed in the reactor 1 in the acetic acid production equipment X as described above. In addition to purifications in the distillation columns 3 and 5, the purification steps include purifications in the distillation column 6 and the ion exchange resin column 7, each of which serves as an additional purification unit, or the purification steps include purifications in the distillation column 6, the ion exchange resin column 7, and the product column, each of which serves as an additional purification unit. The method including such an additional purification step(s) in the additional purification unit(s) is advantageous for high purity of the resulting product acetic acid. The product acetic acid produced by the method has an iodine ion concentration of preferably 10 ppb or less, and more preferably 1 ppb or less and of typically 0.01 ppb or more, or 0.1 ppb or more. The purification step(s), as performed in the additional purification unit(s) with the control of the corrosive iodine concentration to 100 ppm or less, is suitable for restraining corrosion of the unit(s). The purification step(s) as above may eliminate or minimize the use of nickel base alloys and other materials having high corrosion resistance, but being expensive as materials to constitute the inner wall of the unit(s) with which the step(s) is performed. Details of this will be illustrated in the working examples. In addition, the purification step(s), when performed, may decrease the amount of the corrosion-resistant materials to be used in the acetic acid production equipment X.

As described above, the acetic acid production method is suitable for restraining corrosion of the acetic acid production equipment X. The acetic acid production method, which is suitable for restraining corrosion of the acetic acid production equipment X, is also suitable for eliminating or minimizing the use of such expensive corrosion-resistant materials in the equipment, to decrease cost in acetic acid production.

EXAMPLES

The present invention will be illustrated in further detail with reference to several examples below. It should be noted, however, that the examples are never intended to limit the scope of the present invention.

Example 1

Acetic acid was produced using the acetic acid production equipment X illustrated in the FIGURE. In this process, the equipment was operated so that the second acetic acid stream from the distillation column 5, which serves as a dehydration column, included, as a composition, 510 ppm of water, 105 ppm of propionic acid, 1 ppm of methyl acetate, 17 ppm of formic acid, 100 ppb of hydrogen iodide, 120 ppb of iodine ion, 5 ppb of methyl iodide, 10 ppb of hexyl iodide, and 49 ppm of potassium in the form of potassium oxide, with the remainder approximately being acetic acid. In the production process, the second acetic acid stream from the distillation column 5 was introduced into the distillation column 6, which serves as a high-boiling component removing column, and subjected to distillation (third distillation step) therein. The distillation column 6 used herein was a 12-plate column (column including 12 plates). The distillation in the distillation column 6 was performed in the following manner. The second acetic acid stream from the distillation column 5 was introduced into the distillation column 6 at the third plate from bottom at a rate of 1005 grams per hour; and a side stream (third acetic acid stream) was drawn out of the distillation column 6 at the sixth plate from the bottom at a rate of 998 grams per hour. Of an overhead stream from the column top, a part as a distillate was removed or drawn in an amount (removed distillate amount) of 6 grams per hour; and another part was refluxed at a reflux rate of 810 grams per hour. A bottom liquid was drawn out at a rate of 1 gram per hour. During the distillation in the distillation column 6, the column top pressure was controlled within the range of 75 to 80 kPa (gauge pressure); the bottom pressure was controlled within the range of 95 to 100 kPa (gauge pressure), which is higher than the column top pressure; the column top temperature was regulated to 82° C.; and the bottom temperature was regulated to 147° C.

The distillate formed as a result of the distillation in the distillation column 6 was sampled and subjected to a corrosivity evaluation test as follows, where the test simulated the distillation in the distillation column 6. Initially, an autoclave equipped with a zirconium pressure-tight case was prepared, 500 ml of the distillate as a testing liquid was charged into the pressure-tight case, test pieces having a size of 36 mm by 25 mm by 2.5 mm were placed in the testing liquid, and the autoclave was lidded. Separately, the testing liquid before testing was subjected to a chemical composition analysis. Results of the chemical composition analysis before the corrosivity test are presented in Table 1. A material to constitute the test pieces was selected from zirconium (Zr), a nickel base alloy (trade name HASTELLOY C, supplied by Oda Koki Co., Ltd.), a steel-use stainless (SUS) 444 (supplied by Morimatsu Industry Co., Ltd.), which is a 18Cr-2Mo high-purity ferritic stainless steel, and a steel-use stainless (SUS) 316 (supplied by UMETOKU Inc.). Next, the testing liquid in the autoclave was purged with nitrogen to an oxygen concentration of 1 ppm or less. Subsequently, the interior of the autoclave was pressurized to 30 kPa (gauge pressure) by nitrogen introduction, raised in temperature up to 135° C. by heating on an oil bath, and the static pressure after temperature rise was set at 90 kPa (gauge pressure). After a lapse of 500 hours under the static conditions (static temperature and static pressure), the interior of the autoclave was cooled down to room temperature, and part of the testing liquid was sampled from the nozzle of the autoclave, followed by the chemical composition analysis of the sampled liquid. Table 1 also presents results of the chemical composition analysis after the corrosivity test.

The autoclave after the cooling process was purged with nitrogen and was uncovered, from which the test pieces were retrieved and weighed in mass. On the basis of results of the measurements, the thickness reduction rates or corrosion rates (in millimeter (mm) per year) of the test pieces were calculated. The corrosion rate corresponds to reduction in thickness (mm) of each test piece per year. The test pieces were each visually examined to determine whether they suffered from local corrosion (including pitting corrosion).

The results of the corrosivity evaluation test are presented in Table 3. In Table 3, the nickel base alloy is indicated as "HC".

Example 2

Acetic acid was produced using the acetic acid production equipment X by a procedure similar to that in Example 1, except for performing the distillation in the distillation column 6 as follows. Specifically, the distillate was removed from the column top in an amount (removed distillate amount) of 60 grams per hour instead of 6 grams per hour, and the side stream (third acetic acid stream) was drawn from the distillation column 6 in an amount of 944 grams per hour instead of 998 grams per hour. Except for using a distillate formed herein in the distillation in the distillation column 6, a corrosivity evaluation test was performed by a procedure similar to that in Example 1. Results of the chemical composition analyses in Example 2 are presented in Table 1, and results of the corrosion rate measurements and the visual examinations in Example 2 are presented in Table 3. This is the same also for Examples 3 to 6 as follows.

Example 3

Acetic acid was produced using the acetic acid production equipment X by a procedure similar to that in Example 1; and a corrosivity evaluation test was performed by a procedure similar to that in Example 1, except for using a testing liquid having a methanol concentration of 200 ppm, where the testing liquid was prepared by adding methanol to the distillate to be subjected to the corrosivity evaluation test.

Example 4

Acetic acid was produced using the acetic acid production equipment X by a procedure similar to that in Example 1; and a corrosivity evaluation test was performed by a procedure similar to that in Example 1, except for using a testing liquid having a potassium concentration of 42 ppm, where the testing liquid was prepared by adding potassium hydroxide to the distillate to be subjected to the corrosivity evaluation test.

Example 5

Acetic acid was produced using the acetic acid production equipment X by a procedure similar to that in Example 1, except that the second acetic acid stream from the distillation column 5 had a different chemical composition, where the distillation column serves as a dehydration column; that the distillate was removed in a different amount (removed distillate amount) from the distillation column 6; and that the side stream (third acetic acid stream) was drawn from the distillation column 6 in a different amount. The second acetic acid stream in Example 5 included 510 ppm of water, 105 ppm of propionic acid, 1 ppm of methyl acetate, 17 ppm of formic acid, 10 ppb of hydrogen iodide, 14 ppb of iodine ion, 5 ppb of methyl iodide, 10 ppb of hexyl iodide, and 49 ppm of potassium in the form of potassium acetate, with the remainder approximately being acetic acid. In Example 5, the distillate was removed from the distillation column 6 in an amount (removed distillate amount) of 60 grams per hour, and the side stream was drawn from the distillation column 6 in an amount of 944 grams per hour. Using the distillate formed in the distillation in the distillation column 6, a corrosivity evaluation test was performed by a procedure similar to that in Example 1.

Example 6

Acetic acid was produced using the acetic acid production equipment X by a procedure similar to that in Example 5; and a corrosivity evaluation test was performed by a procedure similar to that in Example 1, except for performing the test at a static temperature and a static pressure of 150° C. and 200 kPa (gauge pressure) respectively instead of 135° C. and 90 kPa (gauge pressure).

Example 7

A corrosivity evaluation test was performed by a procedure similar to that in Example 1, except for using another testing liquid instead of the distillate obtained from the distillation column 6 in the acetic acid production process using the acetic acid production equipment X. The other testing liquid included, as a composition, 0.05 mass percent of water, 100 ppm of propionic acid, 5 ppm of methyl acetate, 20 ppm of formic acid, 0.01 ppm of hydrogen iodide, 0.02 ppm of iodine ion, 5 ppb of methyl iodide, and 5 ppb of hexyl iodide, with the remainder approximately being acetic acid. Results of chemical composition analyses in Example 7 are given in Table 2, and results of the corrosion rate measurements and visual examinations in Example 7 are given in Table 3. This is the same for Example 8 and Comparative Examples 1 to 3 below.

Example 8

A corrosivity evaluation test was performed by a procedure similar to that in Example 1, except for using another testing liquid instead of the distillate obtained from the distillation column 6 in the acetic acid production process using the acetic acid production equipment X, and for performing the corrosivity evaluation test at a static temperature of 118° C. instead of 135° C. The other testing liquid included, as a composition, 0.05 mass percent of water, 100 ppm of propionic acid, 5 ppm of methyl acetate, 20 ppm of formic acid, 0.01 ppm of hydrogen iodide, 0.02 ppm of iodine ion, 5 ppb of methyl iodide, and 5 ppb of hexyl iodide, with the remainder approximately being acetic acid.

Comparative Example 1

Acetic acid was produced using the acetic acid production equipment X by a procedure similar to that in Example 1, except that the second acetic acid stream from the distillation column 5 had a different chemical composition, where the distillation column 5 serves as a dehydration column. The second acetic acid stream in Comparative Example 1 included 510 ppm of water, 105 ppm of propionic acid, 1 ppm of methyl acetate, 17 ppm of formic acid, 990 ppb of hydrogen iodide, 1050 ppb of iodine ion, 5 ppb of methyl iodide, 10 ppb of hexyl iodide, and 49 ppm of potassium in the form of potassium acetate, with the remainder approximately being acetic acid. Except for using a distillate formed herein in the distillation in the distillation column 6, a corrosivity evaluation test was performed by a procedure similar to that in Example 1.

Comparative Example 2

A corrosivity evaluation test was performed by a procedure similar to that in Example 1, except for using another testing liquid instead of the distillate obtained from the distillation column 6 in the acetic acid production process using the acetic acid production equipment X. The other testing liquid included, as a composition, 0.0005 mass percent of water, 30 ppm of propionic acid, 103 ppm of methyl acetate, 655 ppm of formic acid, 120 ppm of hydrogen iodide, 134 ppm of iodine ion, 595 ppb of methyl iodide, and 8 ppb of hexyl iodide, with the remainder approximately being acetic acid.

Comparative Example 3

A corrosivity evaluation test was performed by a procedure similar to that in Example 1, except for using another testing liquid instead of the distillate obtained from the distillation column 6 in the acetic acid production process using the acetic acid production equipment X. The other testing liquid included, as a composition, 2.1 mass percent of water, 29 ppm of propionic acid, 102 ppm of methyl acetate, 650 ppm of formic acid, 118 ppm of hydrogen iodide, 132 ppm of iodine ion, 590 ppb of methyl iodide, and 8 ppb of hexyl iodide, with the remainder approximately being acetic acid.

EVALUATIONS

In the corrosivity evaluation tests, materials may be evaluated as follows in terms of thickness reduction (weight loss). A material having a corrosion rate under the predetermined conditions of 0.05 mm per year or less may be evaluated as suitably usable as an inner wall constitutional material for purification units that are exposed to the conditions; a material having a corrosion rate under the predetermined conditions of from greater than 0.05 mm per year to less than 0.2 mm per year may be evaluated as usable as an inner wall constitutional material for purification units that are exposed to the conditions; and a material having a corrosion rate under the predetermined conditions of 0.2 mm per year or more may be evaluated as unsuitable for the use as an inner wall constitutional material for purification units that are exposed to the conditions. On the basis of these, the evaluation results demonstrated that, of the materials, SUS 444 and SUS 316 are unsuitable for use under the conditions according to Comparative Examples 1 to 3, in which the corrosive iodine concentration (total of the hydrogen iodide concentration and the iodine ion concentration) was greater than 100 ppm. These materials are unsuitable from the viewpoint of thickness reduction or corrosion rate. In addition, the material HASTELLOY C ("HC", the nickel base alloy) suffered from local corrosion under all the conditions according to Comparative Examples 1 to 3. Separately, there is a tendency that ionization of hydrogen iodide and acetic acid is restrained with a decreasing water concentration in a liquid to be treated; and that the ionization restrainment acts advantageously on corrosion restrainment. The tendency as above is found in the corrosivity evaluation test results in Comparative Examples 1 and 3. Specifically, materials HC, SUS 444, and SUS 316 in Comparative Example 3 had corrosion rates higher than the corresponding corrosion rates in Comparative Example 1, where the corrosivity evaluation test in Comparative Example 3 was performed at a significantly higher water concentration as compared with Comparative Example 1. In contrast, zirconium (Zr) and SUS 444 in Comparative Example 2 had corrosion rates higher than the corresponding corrosion rates in Comparative Examples 1 and 3, where the corrosivity evaluation test in Comparative Example 2 was performed at a very low water concentration, and where zirconium may be used as a material having very high corrosion resistance. This is probably because of a tendency that a passive film is not appropriately formed on the material surface under such conditions with a very low water concentration.

In contrast, the nickel base alloy HC was evaluated as a suitably usable material from the viewpoint of corrosion rate and offered no local corrosion in all of Examples 1 to 8, where the corrosivity evaluation tests in Examples 1 to 8 were performed at corrosive iodine concentrations (total of the hydrogen iodide concentration and the iodine ion concentration) of 100 ppm or less. SUS 444 was evaluated as a suitably usable material from the viewpoint of corrosion rate and offered approximately no local corrosion in Examples 2 to 5, 7, and 8; and was evaluated as a usable material from the viewpoint of corrosion rate and offered no local corrosion in Examples 1 and 6. SUS 316 was evaluated as a suitably usable material from the viewpoint of corrosion rate and offered no local corrosion in Examples 2 to 5, 7, 8; was evaluated as a usable material from the viewpoint of corrosion rate in Example 1; and was evaluated as a usable material from the viewpoint of corrosion rate and offered no local corrosion in Example 6. Comparisons made in the corrosivity evaluation test results demonstrate as follows. Comparisons between Example 1 and Example 2 demonstrate that corrosion tends to be restrained with an increasing amount (removed distillate amount) of the distillate removed from the overhead stream from the top of the distillation column 6. Comparisons between Example 1 and Example 3 demonstrate that corrosion tends to be restrained by the addition of methanol to the liquid to be treated. Comparisons between Example 1 and Example 4 demonstrate that corrosion tends to be restrained by the addition of potassium hydroxide to the liquid to be treated. Comparisons between Example 2 and Example 5 demonstrate that corrosion tends to be restrained by decreasing the hydrogen iodide concentration in the acetic acid stream upon introduction into the distillation column 6. Comparisons between Example 5 and Example 6 demonstrate that corrosion tends to be restrained under conditions at a lower temperature and a lower pressure. Comparisons between Example 7 and Example 8 demonstrate that corrosion tends to be restrained under conditions at a lower temperature. Zr and SUS 444 in Example 7 had corrosion rates higher than the corresponding corrosion rates typically in Example 5. This is probably because of a tendency that a passive film is not appropriately formed on the material surface under such conditions at a very low water concentration.

TABLE 1

|  | Example 1 | | Example 2 | | Example 3 | |
| --- | --- | --- | --- | --- | --- | --- |
|  | Before test | After test | Before test | After test | Before test | After test |
| Water (mass percent) | 0.34 | 0.34 | 0.34 | 0.34 | 0.34 | 0.35 |
| Propionic acid (ppm) | 30 | 33 | 20 | 22 | 30 | 31 |
| Methyl acetate (ppm) | 105 | 90 | 10 | 7 | 105 | 490 |

TABLE 1-continued

|  | | | | | | |
|---|---|---|---|---|---|---|
| Methanol (ppm) | 1> | 1> | 1> | 1> | 200 | 1> |
| Formic acid (ppm) | 660 | 600 | 90 | 70 | 660 | 590 |
| Hydrogen iodide (ppm) | 14 | 13 | 1.5 | 1.2 | 14 | 1.5 |
| Iodine ion (ppm) | 16 | 14 | 1.9 | 1.7 | 15 | 2.1 |
| Methyl iodide (ppb) | 600 | 400 | 70 | 40 | 600 | 2100 |
| Hexyl iodide (ppb) | 9 | 8 | 9 | 7 | 9 | 8 |
| Potassium (ppm) | 1> | 1> | 1> | 1> | 1> | 1> |
| Acetic acid | Remainder | Remainder | Remainder | Remainder | Remainder | Remainder |
| Temperature (° C.) | 135 | | 135 | | 135 | |
| Pressure (kPaG) | 90 | | 90 | | 90 | |

|  | Example 4 | | Example 5 | | Example 6 | |
|---|---|---|---|---|---|---|
|  | Before test | After test | Before test | After test | Before test | After test |
| Water (mass percent) | 0.34 | 0.35 | 0.34 | 0.34 | 0.34 | 0.34 |
| Propionic acid (ppm) | 30 | 30 | 20 | 19 | 20 | 19 |
| Methyl acetate (ppm) | 105 | 99 | 10 | 8 | 10 | 7 |
| Methanol (ppm) | 1> | 1> | 1> | 1> | 1> | 1> |
| Formic acid (ppm) | 660 | 600 | 90 | 65 | 90 | 59 |
| Hydrogen iodide (ppm) | 14 | 0.5 | 0.11 | 0.09 | 0.11 | 0.08 |
| Iodine ion (ppm) | 15 | 1.0 | 0.15 | 0.13 | 0.15 | 0.14 |
| Methyl iodide (ppb) | 600 | 530 | 70 | 61 | 70 | 55 |
| Hexyl iodide (ppb) | 9 | 8 | 9 | 9 | 9 | 9 |
| Potassium (ppm) | 42 | 43 | 1> | 1> | 1> | 1> |
| Acetic acid | Remainder | Remainder | Remainder | Remainder | Remainder | Remainder |
| Temperature (° C.) | 135 | | 135 | | 150 | |
| Pressure (kPaG) | 90 | | 90 | | 200 | |

TABLE 2

|  | Example 7 | | Example 8 | | Comparative Example 1 | | Comparative Example 2 | | Comparative Example 3 | |
|---|---|---|---|---|---|---|---|---|---|---|
|  | Before test | After test | Before test | After test | Before test | After test | Before test | After test | Before test | After test |
| Water (mass percent) | 0.05 | 0.05 | 0.05 | 0.05 | 0.34 | 0.34 | 0.0005 | 0.0005 | 2.1 | 2.1 |
| Propionic acid (ppm) | 100 | 101 | 100 | 99 | 30 | 28 | 30 | 30 | 29 | 30 |
| Methyl acetate (ppm) | 5 | 4 | 5 | 4 | 105 | 85 | 103 | 86 | 102 | 81 |
| Methanol (ppm) | 1> | 1> | 1> | 1> | 1> | 1> | 1> | 1> | 1> | 1> |
| Formic acid (ppm) | 20 | 15 | 20 | 17 | 660 | 600 | 655 | 610 | 650 | 610 |
| Hydrogen iodide (ppm) | 0.01 | 0.002 | 0.01 | 0.007 | 130 | 110 | 120 | 108 | 118 | 109 |
| Iodine ion (ppm) | 0.02 | 0.015 | 0.02 | 0.018 | 135 | 120 | 134 | 120 | 132 | 121 |
| Methyl iodide (ppb) | 5 | 1 | 5 | 2 | 600 | 650 | 595 | 600 | 590 | 580 |
| Hexyl iodide (ppb) | 5 | 1 | 5 | 2 | 9 | 8 | 8 | 7 | 8 | 6 |
| Potassium (ppm) | 1> | 1> | 1> | 1> | 1> | 1> | 1> | 1> | 1> | 1> |
| Acetic acid | Remainder | Remainder | Remainder | Remainder | Remainder | Remainder | Remainder | Remainder | Remainder | Remainder |
| Temperature (° C.) | 135 | | 118 | | 135 | | 135 | | 135 | |
| Pressure (kPa) | 90 | | 90 | | 90 | | 90 | | 90 | |

TABLE 3

|  |  | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|---|
| Zr | Corrosion rate (mm/year) | 0.00 | 0.00 | 0.00 | 0.00 | 0.00 | 0.00 | 0.01 | 0.005 | 0.00 | 0.06 | 0.00 |
|  | Local corrosion | Absent | Absent | Absent | Absent | Absent | Absent | Absent | Absent | Absent | Absent | Absent |
| HC | Corrosion rate (mm/year) | 0.04 | 0.01 | 0.01 | 0.01 | 0.00 | 0.02 | 0.00 | 0.00 | 0.09 | 0.09 | 0.13 |
|  | Local corrosion | Absent | Absent | Absent | Absent | Absent | Absent | Absent | Absent | Present | Present | Present |
| SUS 444 | Corrosion rate (mm/year) | 0.10 | 0.02 | 0.04 | 0.02 | 0.01 | 0.06 | 0.03 | 0.02 | 0.26 | 0.32 | 0.28 |
|  | Local corrosion | Absent | Absent | Absent | Absent | Absent | Absent | Absent | Absent | Absent | Absent | Absent |
| SUS 316 | Corrosion rate (mm/year) | 0.11 | 0.03 | 0.04 | 0.02 | 0.01 | 0.07 | 0.01 | 0.004 | 0.25 | 0.20 | 0.29 |
|  | Local corrosion | Present | Absent | Absent | Absent | Absent | Absent | Absent | Absent | Present | Present | Present |

The configurations according to the present invention and variations or modifications thereof will be listed below as a summary of the above description.

Appendix 1: A method produces acetic acid in an acetic acid production equipment. The equipment includes a reactor, a first distillation column, a second distillation column, and an additional purification unit. The method includes a reaction step, a first purification step, a second purification step, and a third purification step. In the reaction step, a material mixture including methanol, carbon monoxide, a catalyst, and an iodide is subjected to a methanol carbonylation reaction in the reactor to form acetic acid. In the first purification step, a crude acetic acid stream is subjected to distillation in the first distillation column, where the crude acetic acid stream contains acetic acid formed in the reaction step. The first purification step gives a first acetic acid stream enriched with acetic acid as compared with the crude acetic acid stream. In the second purification step, the first acetic acid stream is subjected to distillation in the second distillation column to give a second acetic acid stream enriched with acetic acid as compared with the first acetic acid stream. In the third purification step, an acetic acid stream is subjected to purification in the additional purification unit while controlling the corrosive iodine concentration in the acetic acid stream passing through the additional purification unit to 100 ppm or less, where the acetic acid stream is the second acetic acid stream or is an acetic acid stream derived from the second acetic acid stream. The third purification step gives a third acetic acid stream enriched with acetic acid as compared with the second acetic acid stream.

Appendix 2: In the acetic acid production method according to appendix 1, the third purification step may include subjecting the acetic acid stream to the purification while controlling the corrosive iodine concentration in the acetic acid stream passing through the additional purification unit to 30 ppm or less.

Appendix 3: In the acetic acid production method according to appendix 1, the third purification step may include subjecting the acetic acid stream to the purification while controlling the corrosive iodine concentration in the acetic acid stream passing through the additional purification unit to 10 ppm or less.

Appendix 4: In the acetic acid production method according to appendix 1, the third purification step may include subjecting the acetic acid stream to the purification while controlling the corrosive iodine concentration in the acetic acid stream passing through the additional purification unit to 3.5 ppm or less.

Appendix 5: In the acetic acid production method according to appendix 1, the third purification step may include subjecting the acetic acid stream to the purification while controlling the corrosive iodine concentration in the acetic acid stream passing through the additional purification unit to 1 ppm or less.

Appendix 6: In the acetic acid production method according to appendix 1, the third purification step may include subjecting the acetic acid stream to the purification while controlling the corrosive iodine concentration in the acetic acid stream passing through the additional purification unit to 0.3 ppm or less.

Appendix 7: In the acetic acid production method according to appendix 1, the third purification step may include subjecting the acetic acid stream to the purification while controlling the corrosive iodine concentration in the acetic acid stream passing through the additional purification unit to 0.1 ppm or less.

Appendix 8: In the acetic acid production method according to appendix 1, the third purification step may include subjecting the acetic acid stream to the purification while controlling the corrosive iodine concentration in the acetic acid stream passing through the additional purification unit to 0.03 ppm or less.

Appendix 9: In the acetic acid production method according to any one of appendixes 1 to 8, the additional purification unit may include a third distillation column, and the third purification step may include subjecting the acetic acid stream to distillation in the third distillation column.

Appendix 10: In the acetic acid production method according to appendix 9, the third purification step may include feeding at least one substance selected from the group consisting of methanol, methyl acetate, and potassium hydroxide to the acetic acid stream under the distillation in the third distillation column.

Appendix 11: In the acetic acid production method according to appendix 10, the methanol may be fed to the acetic acid stream under the distillation in the third distillation column at a level equal to or lower than the level at which the acetic acid stream is introduced into the third distillation column, where the levels are defined with respect to the height direction of the third distillation column.

Appendix 12: In the acetic acid production method according to one of appendixes 10 and 11, the methyl acetate may be fed to the acetic acid stream under the distillation in the third distillation column at a level equal to or lower than the level at which the acetic acid stream is introduced into the third distillation column, where the levels are defined with respect to the height direction of the third distillation column.

Appendix 13: In the acetic acid production method according to any one of appendixes 10 to 12, the potassium hydroxide may be fed to the acetic acid stream under the distillation in the third distillation column at a level equal to or higher than the level at which the acetic acid stream is introduced into the third distillation column, where the levels are defined with respect to the height direction of the third distillation column.

Appendix 14: In the acetic acid production method according to any one of appendixes 9 to 13, the third purification step may include at least one selected from the group consisting of recycling part of an overhead from the third distillation column to the first acetic acid stream before being introduced into the second distillation column, and recycling part of the overhead from the third distillation column to the crude acetic acid stream before being introduced into the first distillation column, so as to control the corrosive iodine concentration.

Appendix 15: In the acetic acid production method according to any one of appendixes 9 to 14, the acetic acid production equipment may further include a scrubber system. The scrubber system treats part of gaseous components evolved in the equipment to form a component to be recycled to the reactor, and a component to be discharged from the equipment.

Appendix 16: The acetic acid production method according to appendix 15 may further include introducing part of an overhead from the third distillation column into the scrubber system.

Appendix 17: In the acetic acid production method according to any one of appendixes 1 to 16, the third purification step may include feeding at least one substance selected from the group consisting of methanol, methyl acetate, and potassium hydroxide to an acetic acid stream before being introduced into the additional purification unit, so as to control the corrosive iodine concentration.

Appendix 18: In the acetic acid production method according to appendix 17, the at least one substance may be fed to the acetic acid stream before being introduced into the additional purification unit so that the acetic acid stream has a corrosive iodine concentration of 100 ppb or less.

Appendix 19: In the acetic acid production method according to any one of appendixes 1 to 18, the acetic acid stream in the additional purification unit may be controlled to have a water concentration of 0.001 mass percent or more.

Appendix 20: In the acetic acid production method according to any one of appendixes 1 to 18, the acetic acid stream in the additional purification unit may be controlled to have a water concentration of 0.003 mass percent or more.

Appendix 21: In the acetic acid production method according to any one of appendixes 1 to 18, the acetic acid stream in the additional purification unit may be controlled to have a water concentration of 0.005 mass percent or more.

Appendix 22: In the acetic acid production method according to any one of appendixes 1 to 18, the acetic acid stream in the additional purification unit may be controlled to have a water concentration of 0.006 mass percent or more.

Appendix 23: In the acetic acid production method according to any one of appendixes 1 to 22, the acetic acid stream in the additional purification unit may be controlled to have a water concentration of 2 mass percent or less.

Appendix 24: In the acetic acid production method according to any one of appendixes 1 to 22, the acetic acid stream in the additional purification unit may be controlled to have a water concentration of 1 mass percent or less.

Appendix 25: In the acetic acid production method according to any one of appendixes 1 to 22, the acetic acid stream in the additional purification unit may be controlled to have a water concentration of 0.5 mass percent or less.

Appendix 26: In the acetic acid production method according to any one of appendixes 1 to 25, the purification in the additional purification unit may be performed at 160° C. or lower.

Appendix 27: In the acetic acid production method according to any one of appendixes 1 to 25, the purification in the additional purification unit may be performed at 150° C. or lower.

Appendix 28: In the acetic acid production method according to any one of appendixes 1 to 25, the purification in the additional purification unit may be performed at 140° C. or lower.

Appendix 29: In the acetic acid production method according to any one of appendixes 1 to 25, the purification in the additional purification unit may be performed at 120° C. or lower.

Appendix 30: In the acetic acid production method according to any one of appendixes 1 to 29, the crude acetic acid stream may have an acetic acid concentration of 87 to 99 mass percent.

Appendix 31: In the acetic acid production method according to any one of appendixes 1 to 30, the acetic acid concentration in the first acetic acid stream may be higher than the acetic acid concentration in the crude acetic acid stream and may be 99 to 99.9 mass percent.

Appendix 32: In the acetic acid production method according to any one of appendixes 1 to 31, the acetic acid concentration in the second acetic acid stream may be higher than the acetic acid concentration in the first acetic acid stream and may be 99.1 to 99.99 mass percent.

Appendix 33: In the acetic acid production method according to any one of appendixes 1 to 32, the acetic acid concentration in the third acetic acid stream may be higher than the acetic acid concentration in the second acetic acid stream and may be 99.8 to 99.999 mass percent.

REFERENCE SIGNS LIST 1 reactor
2 evaporator
3 distillation column (first distillation column)
4 decanter
5 distillation column (second distillation column)
6 distillation column (third distillation column; additional purification unit)
7 ion exchange resin column (additional purification unit)
8 scrubber system

The invention claimed is:
1. A method for producing acetic acid in acetic acid production equipment, the equipment comprising:
 a reactor;
 a first distillation column;
 a second distillation column; and
 an additional purification unit,
 the method comprising:
 a reaction step of subjecting a material mixture comprising methanol, carbon monoxide, a catalyst, and an iodide to a methanol carbonylation reaction in the reactor to form acetic acid in a reaction mixture;
 a flash evaporation step of partially evaporating the reaction mixture into vapors and residual liquid components, wherein a portion of the vapors is introduced into the first distillation column as a crude acetic acid stream;
 a first purification step of subjecting the crude acetic acid stream to distillation in the first distillation column to give a first acetic acid stream, the crude acetic acid stream containing the acetic acid formed in the reaction step, the first acetic acid stream being enriched with acetic acid as compared with the crude acetic acid stream;
 a second purification step of subjecting the first acetic acid stream to distillation in the second distillation column to give a second acetic acid stream enriched with acetic acid as compared with the first acetic acid stream; and
 a third purification step of subjecting an acetic acid stream to purification in the additional purification unit while controlling a corrosive iodine concentration in the acetic acid stream passing through the additional purification unit to 100 ppm or less, to give a third acetic acid stream enriched with acetic acid as compared with the second acetic acid stream,
 wherein an acetic acid concentration in the second acetic acid stream is higher than an acetic acid concentration in the first acetic acid stream and is 99.1 to 99.99 mass percent.
2. The method according to claim 1,
 wherein the additional purification unit comprises a third distillation column, and
 wherein the third purification step comprises performing distillation in the third distillation column.
3. The method according to claim 2,
 wherein the third purification step comprises
 feeding at least one substance selected from the group consisting of methanol, methyl acetate, and potassium hydroxide to the acetic acid stream under the distillation in the third distillation column, so as to control the corrosive iodine concentration.

4. The method according to claim 3,
wherein the methanol is fed to the acetic acid stream under the distillation in the third distillation column at a level equal to or lower than a level at which the acetic acid stream is introduced into the third distillation column, where the levels are defined with respect to a height direction of the third distillation column.

5. The method according to claim 3,
wherein the methyl acetate is fed to the acetic acid stream under the distillation in the third distillation column at a level equal to or lower than a level at which the acetic acid stream is introduced into the third distillation column, where the levels are defined with respect to a height direction of the third distillation column.

6. The method according to claim 3,
wherein the potassium hydroxide is fed to the acetic acid stream under the distillation in the third distillation column at a level equal to or higher than a level at which the acetic acid stream is introduced into the third distillation column, where the levels are defined with respect to a height direction of the third distillation column.

7. The method according to claim 2,
wherein the third purification step comprises at least one selected from the group consisting of:
recycling part of an overhead from the third distillation column to the first acetic acid stream before being introduced into the second distillation column; and
recycling part of the overhead from the third distillation column to the crude acetic acid stream before being introduced into the first distillation column, so as to control the corrosive iodine concentration.

8. The method according to claim 2,
wherein the acetic acid production equipment further comprises
a scrubber system that treats part of gaseous components evolved in the equipment to form a component to be recycled to the reactor, and a component to be discharged from the equipment.

9. The method according to claim 8, the method further comprising
introducing part of an overhead from the third distillation column into the scrubber system.

10. The method according to claim 1,
wherein the third purification step comprises
feeding at least one substance selected from the group consisting of methanol, methyl acetate, and potassium hydroxide to an acetic acid stream before being introduced into the additional purification unit.

11. The method according to claim 10,
wherein the at least one substance is fed to the acetic acid stream before being introduced into the additional purification unit so that the acetic acid stream has a corrosive iodine concentration of 100 ppb or less.

12. The method according to claim 1,
wherein the acetic acid stream in the additional purification unit has a water concentration of 0.001 mass percent or more.

13. The method according to claim 1,
wherein the acetic acid stream in the additional purification unit has a water concentration of 2 mass percent or less.

14. The method according to claim 1,
wherein the third purification step comprises
performing the purification in the additional purification unit at a temperature of 160° C. or lower.

15. The method according to claim 4,
wherein the methyl acetate is fed to the acetic acid stream under the distillation in the third distillation column at a level equal to or lower than a level at which the acetic acid stream is introduced into the third distillation column, where the levels are defined with respect to a height direction of the third distillation column.

16. A method for producing acetic acid in acetic acid production equipment, the equipment comprising:
a reactor;
a first distillation column;
a second distillation column; and
an additional purification unit,
the method comprising:
a reaction step of subjecting a material mixture comprising methanol, carbon monoxide, a catalyst, and an iodide to a methanol carbonylation reaction in the reactor to form acetic acid in a reaction mixture;
a first purification step of subjecting a crude acetic acid stream to distillation in the first distillation column to give a first acetic acid stream, the crude acetic acid stream containing the acetic acid formed in the reaction step, the first acetic acid stream being enriched with acetic acid as compared with the crude acetic acid stream;
a second purification step of subjecting the first acetic acid stream to distillation in the second distillation column to give a second acetic acid stream enriched with acetic acid as compared with the first acetic acid stream; and
a third purification step of subjecting an acetic acid stream to purification in the additional purification unit while controlling a corrosive iodine concentration in the acetic acid stream having a water concentration of 0.001 to 2 mass percent and passing through the additional purification unit to 100 ppm or less, to give a third acetic acid stream enriched with acetic acid as compared with the second acetic acid stream,
wherein an acetic acid concentration in the second acetic acid stream is higher than an acetic acid concentration in the first acetic acid stream and is 99.1 to 99.99 mass percent.

17. The method according to claim 16, further comprising a flash evaporation step of partially evaporating the reaction mixture into vapors and residual liquid components, wherein a portion of the vapors is introduced into the first distillation column as a crude acetic acid stream.

18. The method according to claim 1,
wherein the third purification step comprises
subjecting the acetic acid stream to the purification in the additional purification unit while controlling the corrosive iodine concentration in the acetic acid stream passing through the additional purification unit to 30 ppm or less, to give the third acetic acid stream.

19. The method according to claim 16,
wherein the third purification step comprises
subjecting the acetic acid stream to the purification in the additional purification unit while controlling the corrosive iodine concentration in the acetic acid stream having the water concentration of 0.001 to 2 mass percent and passing through the additional purification unit to 30 ppm or less, to give the third acetic acid stream.

20. The method according to claim 1,
wherein the crude acetic acid stream has an acetic acid concentration of 87 to 99 mass percent.

21. The method according to claim 1,
wherein an acetic acid concentration in the first acetic acid stream is higher than an acetic acid concentration in the crude acetic acid stream and is 99 to 99.9 mass percent.

22. The method according to claim 1,
wherein an acetic acid concentration in the third acetic acid stream is higher than an acetic acid concentration in the second acetic acid stream and is 99.8 to 99.999 mass percent.

23. The method according to claim 16,
wherein the crude acetic acid stream has an acetic acid concentration of 87 to 99 mass percent.

24. The method according to claim 16,
wherein an acetic acid concentration in the first acetic acid stream is higher than an acetic acid concentration in the crude acetic acid stream and is 99 to 99.9 mass percent.

25. The method according to claim 16,
wherein an acetic acid concentration in the third acetic acid stream is higher than an acetic acid concentration in the second acetic acid stream and is 99.8 to 99.999 mass percent.

26. A method for producing acetic acid in acetic acid production equipment, the equipment comprising:
a reactor;
a first distillation column;
a second distillation column; and
an additional purification unit,
the method comprising:
a reaction step of subjecting a material mixture comprising methanol, carbon monoxide, a catalyst, and an iodide to a methanol carbonylation reaction in the reactor to form acetic acid in a reaction mixture;
a flash evaporation step of partially evaporating the reaction mixture into vapors and residual liquid components, wherein a portion of the vapors is introduced into the first distillation column as a crude acetic acid stream;
a first purification step of subjecting the crude acetic acid stream to distillation in the first distillation column to give a first acetic acid stream, the crude acetic acid stream containing the acetic acid formed in the reaction step, the first acetic acid stream being enriched with acetic acid as compared with the crude acetic acid stream;
a second purification step of subjecting the first acetic acid stream to distillation in the second distillation column to give a second acetic acid stream enriched with acetic acid as compared with the first acetic acid stream; and
a third purification step of subjecting an acetic acid stream to purification in the additional purification unit while controlling a corrosive iodine concentration in the acetic acid stream passing through the additional purification unit to 100 ppm or less, to give a third acetic acid stream enriched with acetic acid as compared with the second acetic acid stream,
wherein an acetic acid concentration in the third acetic acid stream is higher than an acetic acid concentration in the second acetic acid stream and is 99.8 to 99.999 mass percent.

* * * * *